(12) United States Patent
Gierskcky et al.

(10) Patent No.: US 6,992,107 B1
(45) Date of Patent: Jan. 31, 2006

(54) ESTERS OF 5-AMINOLEVULINIC ACID AND THEIR USE AS PHOTOSENSITIZING COMPOUNDS IN PHOTOCHEMOTHERAPY

(75) Inventors: Karl E. Gierskcky, Oslo (NO); Johan Moan, Oslo (NO); Qian Peng, Oslo (NO); Harald Steen, Oslo (NO); Trond Warloe, Oslo (NO); Alf Bjorseth, Glomfjord (NO)

(73) Assignee: Photocure ASA, Oslo (NO)

( * ) Notice: Subject to any disclaimer, the term of this patent is extended or adjusted under 35 U.S.C. 154(b) by 13 days.

(21) Appl. No.: 09/655,570

(22) Filed: Sep. 6, 2000

Related U.S. Application Data

(63) Continuation-in-part of application No. 09/471,620, filed on Dec. 21, 1999, now Pat. No. 6,492,420, which is a continuation of application No. 08/913,257, filed as application No. PCT/GB96/00553 on Mar. 8, 1997, now Pat. No. 6,034,267.

(30) Foreign Application Priority Data

| Mar. 10, 1995 | (GB) | 9504948 |
|---|---|---|
| Dec. 18, 1995 | (GB) | 9525822 |

(51) Int. Cl.
| A61K 31/22 | (2006.01) |
|---|---|
| A61K 31/21 | (2006.01) |
| C07C 229/00 | (2006.01) |
| B65D 71/00 | (2006.01) |

(52) U.S. Cl. ............... 514/551; 514/506; 560/155; 560/170; 206/569; 206/570

(58) Field of Classification Search ............ 560/155, 560/170; 514/551, 506; 206/569, 570
See application file for complete search history.

(56) References Cited

U.S. PATENT DOCUMENTS

| 4,087,532 A | 5/1978 | Merz et al. |
|---|---|---|
| 4,575,515 A | 3/1986 | Sandborn ............ 514/708 |
| 5,079,262 A | 1/1992 | Kennedy et al. ............ 514/561 |
| 5,211,938 A | 5/1993 | Kennedy et al. ............ 424/7.1 |
| 5,219,878 A | 6/1993 | Ringuet et al. ............ 514/410 |
| 5,234,940 A | 8/1993 | Kennedy et al. ............ 514/410 |
| 5,422,093 A | 6/1995 | Kennedy et al. ............ 424/9.61 |
| 5,661,111 A * | 8/1997 | Kuramochi et al. |
| 5,955,490 A | 9/1999 | Kennedy et al. |
| 6,034,267 A * | 3/2000 | Gierskcky et al. ............ 560/155 |
| 6,492,420 B2 * | 12/2002 | Gierskcky et al. ............ 514/551 |

FOREIGN PATENT DOCUMENTS

| DE | 2411382 | | 9/1975 |
|---|---|---|---|
| EP | 0316179 | | 5/1989 |
| GB | 1 496 418 | | 12/1977 |
| GB | 2058077 A | | 4/1981 |
| HU | 197211 | | 1/1990 |
| JP | 04-009360 | * | 1/1992 |
| JP | 07-053487 | * | 2/1995 |
| WO | 91/01727 | | 2/1991 |
| WO | 92/06097 | | 4/1992 |
| WO | 93/20810 | | 10/1993 |
| WO | 95/07077 | | 3/1995 |
| WO | WO 96/28412 | | 9/1996 |

OTHER PUBLICATIONS

Database Xfire, entries 3060978, 5347132, 5499790, 5620924, 5633390, 5991317 and 6517740, Beilstein XP002005286.

*Chemical Abstracts, 16*, Abstract of Japanese Patent Application No. JP900287712 (Haruhiko), published Jan. 14, 1992, from, (Apr. 16, 1992).

Ariens, E.J., "Drug Design", *Academic Press, New York*, 8–11, 70–71, (1971).

Cotton, F.A., et al., "Advanced Inorganic Chemistry", *5th ed., Wiley, New York*, 305–309, 382–386, (1988).

Davies, A.G., "Organic Peroxides", *Butterworth and Co., London*, 196, (1961).

Dougherty, T.J., "Activated Dyes as Antitumor Agents", *Journal of the National Cancer Institute*, 52, 1333–1336, (Apr. 1974).

Kelly, J.F., et al., "Hematoporphyrin Derivative: A Possible Aid in the Diagnosis and Therapy of Carcinoma of the Bladder", *The Journal of Urology*, 115, Copyrighted 1976 by The Williams & Wilkins Co., 150–151, (Feb.).

Cellular porphyrin formation

Kloek, J., et al., "Prodrugs of 5–Aminolevulinic Acid for Photodynamic Therapy", *Photochemistry and Photobiology*, 64(6), 994–1000, (1996).

Qian, P., et al., "A Comparison of Different Photosensitizing Dyes with Respect to Uptake C3H–Tumors and Tissues of Mice", *Cancer Letters*, 36, 1–10, (1987).

Kloek, J., et al.; "Prodrugs of 5–Aminolevulinic Acid for Photodynamic Therapy". Photochemistry and Photobiology. 64(6). 994–1000, (1996).

Whitaker et al., "Photosensitization of pancreatic tumour cells by δ–aminolaevulinic acid esters," Anti–Cancer Drug Design (2000), vol. 15, pp. 161–170.

Davies, A. G.; Organic Peroxides; Butterworth and Co. London. P. 196. 1961.

Cotton, F. A. et al; Advanced Inorganic Chemistry. 5$^{th}$ ed. Wiley. New York; pp. 305–309, 382–386. 1988.

Salerni, O. L. et al.; J. Chem Soc. (C); p. 1400. 1968.

Ariens, E. J.; Drug Design; Academic Press; New York; pp. 8–11, 70–71, .1971.

Morrison, R. T. et al.; Organic Chemistry 3$^{rd}$ Ed.; Allyn and Bacon; Boston; pp. 631, 666, 668–669, 673. 1973.

Gawell, L. et al.; Acta Chemica Scandinavica; 43; p. 478–479. 1989.

Schulz, G. et al.; Chem. Ber.; 113 (2); p. 772. 1980.

Database Xfire entries, Beilstein Registry Nos. 3060978, 5347132, 5499790, 5620924, 5633390, 5991317, 6517740.

Abstract of Japanese Patent Application No. JP900287712 (Haruhiko), published Jan. 14, 1992, Patent Abstracts of Japan, vol. 16, No. 156 (C–0930).

Dougherty, T. J., "Activated Dyes as Antitumor Agents". Journal of the National Cancer Institute, 52, 1333–1336. (Apr. 1974).

Kelly, J. F., et al.; "Hematoporphyrin Derivative: A Possible Aid in the Diagnosis and Therapy of Carcinoma of the Bladder". The Journal of Urology, 115. Copyright 1976 by the Williams and Wilkins Co., 150–151. (Feb.).

Kloek, J., et al.; "Prodrugs of 5–Aminolevulinic Acid for Photodynamic Therapy". Photochemistry and Photobiology. 64(6). 994–1000. (1996).

Qian. P. et al.; "A Comparison of Different Photosensitizing Dyes with Respect to Uptake C3H–Tumors and Tissues of Mice". Cancer Letters. 36. 1–10. (1987).

Abstract of Japanese Patent No. 2000023691 (Jan. 25, 2000), Patent Abstracts of Japan, Unexamined Applications, vol. 2000.

Abstract of Japanese Patent No. 11028084 (Feb. 2, 1999), Patent Abstracts of Japan, Unexamined Applications, vol. 99, No. 2.

Abstract of Japanese Patent No. 11012197 (Jan. 19, 1999), Patent Abstracts of Japan, Unexamined Applications, vol. 99, No. 1.

Abstract of Japanese Patent No. 08151304 (Jun. 11, 1996), Patent Abstracts of Japan, Unexamined Applications, vol. 96, No. 6.

Abstract of Japanese Patent No. 07053487 (Feb. 28, 1995), Patent Abstracts of Japan, Unexamined Applications, vol. 95, No. 2.

Abstract of Japanese Patent No. 06141681 (May 24, 1994), Patent Abstracts of Japan, Unexamined Applications, Section C, Sect. No. 1240, vol. 18, No. 448, p. 103 (Aug. 22, 1994).

Abstract of Japanese Patent No. 05137587 (Jun. 1, 1993), Patent Abstracts of Japan, Unexamined Applications, Section C, Sect. No. 1110, vol. 17, No. 5, p. 13 (Sep. 13, 1993).

Abstract of Japanese Patent No. 11171852 (Jun. 29, 1999), STN Easy.

Chemical Abstract Registry Nos. 79416–27–6, 163271–25–8, 186146–43–0, 163271–24–7, 186410–01–5, 204326–60–3, 140898–97–1, 140898–99–3, 140898–98–2, 140899–00–9, 140899–01–0, 140899–02–1, 163271–28–1, 140899–03–2, 163271–21–4, 163271–26–9, 163271–27–0, 163271–20–3, 123498–44–2, 163271–23–6, 163271–22–5, 186410–02–6, 1864100–3–7.

Y. Berger et al., "Ethylene Glycol and Amino Acid Derivatives of 5–Aminolevulinic Acid as New Photosensitizing Precursors of Protoporphyrin IX in Cells," J. Med. Chem., vol. 43, Dec. 1, 2000, pp. 4738–4746.

* cited by examiner

*Primary Examiner*—Paul A. Zucker
(74) *Attorney, Agent, or Firm*—Kenyon & Kenyon

(57) ABSTRACT

The present invention provides a compound of formula I;

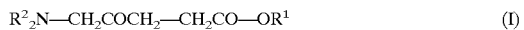

$$R^2{}_2N—CH_2COCH_2—CH_2CO—OR^1 \qquad (I)$$

wherein $R^1$ represents (a) an optionally substituted branched $C_{6-30}$ alkyl group, comprising a straight chain $C_{4-29}$ alkyl group, branched by substitution with one or more $C_{1-6}$ alkyl groups, wherein said site of substitution is at C2 or a higher C atom, (b) a non-heteroaromatic aryl substituted alkyl group, wherein said aryl group is substituted, or (c) an alkoxy substituted alkyl group, wherein said alkoxy group is substituted by a methoxy group or an alkoxy group substituted with an alkoxy group, wherein in (a) and (b) said substituents are selected from hydroxy, alkoxy, acyloxy, alkoxycarbonyloxy, amino, aryl, nitro, oxo or fluoro groups, and said alkyl group is optionally interrupted or terminated by one or more —O—, $NR^3$—, —S— or $PR^3$— groups; $R^2$, each of which may be the same or different, represents a hydrogen atom or a group $R^1$, wherein $R^1$ represents (a) an optionally substituted branched $C_{5-30}$ alkyl group, comprising a straight chain $C_{4-29}$ alkyl group, branched by substitution with one or more $C_{1-6}$ alkyl groups, wherein said site of substitution is at C2 or a higher C atom, (b) a non-heteroaromatic aryl substituted alkyl group, wherein said aryl group is substituted, or (c) an alkoxy substituted alkyl group, wherein said alkoxy group is substituted by a methoxy group or an alkoxy group substituted with an alkoxy group, wherein in (a) and (b) said substituents are selected from hydroxy, alkoxy, acyloxy, alkoxycarbonyloxy, amino, aryl, nitro, oxo or fluoro groups, and said alkyl group is optionally interrupted or terminated by one or more —O—, $NR^3$—, —S— or $PR^3$— groups; and $R^3$ represents a hydrogen or $C_{1-6}$ alkyl group, and salts thereof for use in photochemotherapy or diagnosis. Pharmaceutical compositions comprising said compound, methods of diagnosis or photochemotherapy using said compound and related compounds and compositions, and products and kits comprising said compounds are also provided.

52 Claims, 6 Drawing Sheets

Skin fluorescence after topical application

Skin fluorescence after topical application of new derivatives of ALA.

Skin fluorescence after topical application

Skin fluorescence after topical application

Skin fluorescence - New esters of ALA

Skin fluorescence after topical application

ESTERS OF 5-AMINOLEVULINIC ACID AND THEIR USE AS PHOTOSENSITIZING COMPOUNDS IN PHOTOCHEMOTHERAPY

This application is a Continuation-In-Part of application Ser. No. 09/471,620, filed on Dec. 21, 1999, now issued as U.S. Pat. No. 6,492,420 which in turn is a continuation of application Ser. No. 08/913,257, filed on Dec. 5, 1997, now issued as U.S. Pat. No. 6,034,267, issued on Mar. 7, 2000, which in turn is a U.S. National phase filing under 35 U.S.C. §371 of International Patent Application No. PCT/GB96/00553, filed on Mar. 8, 1996, which in turn is an international filing of British Patent Application No. 9525822.4, filed on Dec. 18, 1995, and of British Patent Application No. 9504948.2, filed on Mar. 10, 1995, all of which are incorporated herein by reference.

The present invention relates to new derivatives of 5-aminolevulinic acid (ALA) and in particular to esters of ALA and their use as photosensitizing agents in photochemotherapy or diagnosis.

Photochemotherapy, or photodynamic therapy (PDT) as it is also known, is a technique for the treatment of various abnormalities or disorders of the skin-or other epithelial organs or mucosa, especially cancers or pre-cancerous lesions, as well as certain non-malignant lesions for example skin complaints such as psoriasis. Photochemotherapy involves the application of photosensitizing (photochemotherapeutic) agents to the affected area of the body, followed by exposure to photoactivating light in order to activate the photosensitizing agents and convert them into cytotoxic form, whereby the affected cells are killed or their proliferative potential diminished.

A range of photosensitizing agents are known, including notably the psoralens, the porphyrins, the chlorins and the phthalocyanins. Such drugs become toxic when exposed to light.

Photosensitizing drugs may exert their effects by a variety of mechanisms, directly or indirectly. Thus for example, certain photo ensitizers become directly toxic when activated by light, whereas others act to generate toxic species, e.g. oxidising agents such as singlet oxygen or other oxygen-derived free radicals, which are extremely destructive to cellular material and biomolecules such as lipids, proteins and nucleic acids. Psoralens are an example of directly acting photosensitizers; upon exposure to light they form adducts and cross-links between the two strands of DNA molecules, thereby inhibiting DNA synthesis. The unfortunate risk with this therapy is that unwanted mutagenic and carcinogenic side effects may occur.

This disadvantage may be avoided by selecting photosensitizers with an alternative, indirect mode of action. For example porphyrins, which act indirectly by generation of toxic oxygen species, have no mutagenic side effects and represent more favourable candidates for photochemotherapy. Porphyrins are naturally occurring precursors in the synthesis of heme. In particular, heme is produced when iron ($Fe^{3+}$) is incorporated in protoporphyrin IX (Pp) by the action of the enzyme ferrochelatase. Pp is an extremely potent photosensitizer, whereas heme has no photosensitizing effect.

One such porphyrin-based drug, Photofrin, has recently been approved as a photosensitizer in the therapy of certain cancers. The main disadvantage is that since it must be administered parenterally, generally intravenously, cause photosensitization of the skin which may last for several weeks following i.v. injection. Photofrin consists of large oligomers of porphyrin and it does not readily penetrate the skin when applied topically. Similar problems exist with other porphyrin-based photosensitizers such as the so-called "hematoporphyrin derivative" (Hpd) which has also been reported for use in cancer photochemotherapy (see for example S. Dougherty. J. Natl. Cancer Ins., 1974, 52; 1333; Kelly and Snell, J. Urol, 1976, 115: 150). Hpd is a complex mixture obtained by treating haematoporphyrin with acetic and sulphuric acids, after which the acetylated product is dissolved with alkali.

To overcome these problems, precursors of Pp have been investigated for photochemotherapeutic potential. In particular the Pp precursor 5-aminolevulinic acid (ALA) has been investigated as a photochemotherapeutic agent for certain skin cancers. ALA, which is formed from succinyl CoA and glycine in the first step of heme synthesis, is to a limited extent able to penetrate the skin and lead to a localised build-up of Pp; since the action of ferrochelatase (the metallating enzyme) is the rate limiting step in heme synthesis, an excess of ALA leads to accumulation of Pp, the photosensitizing agent. Thus, by applying ALA topically to skin tumours, and then after several hours exposing the tumours to light, a beneficial photochemotherapeutic effect may be obtained (see for example WO91/01727). Since the skin covering basilomas and squamous cell carcinomas is more readily penetrated by ALA than healthy skin, and since the concentration of ferrochelatase is low in skin tumours, it has been found that topical application of ALA leads to a selectively enhanced production of Pp in tumours.

However, photochemotherapy with ALA is not always entirely satisfactory. ALA is not able to penetrate all tumours and other tissues with sufficient efficacy to enable treatment of a wide range of tumours or other conditions and ALA also tends to be unstable in pharmaceutical formulations. These problems have to a large extent been overcome by the use of straight chain, unsubstituted alkyl ALA esters which exhibit improved selectivity for abnormal tissue, non-systemic localization of administered agents, improved uptake and PpIx production, and reduced pain sensation on administration (see WO96/28412).

Database Xfire, entries 3060978, 5347132, 5499790, 5620924, 5633390, 5991317 and 6517740 (Beilstein); Cosmo Sogo Kenkyusho KK, Patent Abstracts of Japan, Vol 16; No. 156 (C-0930), 16.4.1992; EP-A-316179 (Tokuyama Soda KK); GB-A-2058077 (Hudson et al) and DE-A-2411382 (Boehringer Sohn Ingelheim) describe alkyl ester derivatives of 5-aminolevulinic acid, and derivatives and salts thereof and processes for their preparation.

However, these compounds still exhibit some limitations for use as pharmaceuticals in PDT, e.g. relative low efficacy, and thus a need therefore exists for improved photochemotherapeutic agents.

The present invention addresses this need and in particular aims to provide photochemotherapeutic agents which are better pharmaceuticals, i.e. which have an enhanced photochemotherapeutic effect over those described in the prior art.

It has now been found that a class of derivatized ALA esters, essentially comprising branched alkyl ALA esters and substituted benzyl ALA esters provide surprisingly advantageous enhanced PDT properties compared to known compounds.

In one aspect, the present invention thus provides compounds of formula I,

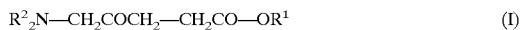

R²₂N—CH₂COCH₂—CH₂CO—OR¹ (I)

(wherein
R¹ represents
an optionally substituted branched $C_{5-30}$ alkyl group, or a substituted alkyl group,
wherein said substituents are selected from hydroxy, alkoxy, acyloxy, alkoxycarbonyloxy, amino, aryl, nitro, oxo or fluoro groups, and said alkylgroup is optionally interrupted or terminated by one or more —O—, NR—, —S— or PR³— groups;
R², each of which may be the same or different, represents a hydrogen atom or a group R¹; and
R³ represents a hydrogen or $C_{1-6}$ alkyl group) and salts thereof for use in photochemotherapy or diagnosis.

As used herein, the term "alkyl", unless stated otherwise, includes any long or short chain, cyclic, straight-chained or branched aliphatic saturated or unsaturated hydrocarbon group. The unsaturated alkyl groups may be mono- or polyunsaturated and include both alkenyland alkynyl group. Unless stated otherwise, such groups may contain up to 40 atoms. However, alkyl groups containing up to 8, especially preferably up to 4. carbon atoms are preferred.

The substituted alkyl R¹ groups may be mono or poly-substituted. Thus suitable R¹ groups include for example alkoxyalkyl, hydroxyalkoxyalkyl, polyhydroxyalkyl, hydroxy poly alkyleneoxyalkyl and the like.

The term "acyl" as used herein includes both carboxylate and carbonate groups, thus, acyloxy substituted alkyl groups include for example alkylcarbonyloxy alkyl. In such groups any alkylene moieties preferably have carbon atom contents defined for alkyl groups below.

Preferred aryl groups include phenyl and monocyclic 5–7 membered heteroaromatics (unless stated otherwise), especially phenyl and such groups may themselves optionally be substituted.

Representative substituted alkyl groups R¹ include acylalkyl, alkoxymethyl, alkoxyethyl and alkoxypropyl groups or acyloxymethyl, acyloxyethyl and acyloxypropyl group e.g. pivaloyloxymethyl.

Preferably said branched alkyl group in formula I is a $C_{5-8}$ straight chain alkyl group which is branched by substitution with one or more optionally substituted $C_{1-6}$ alkyl groups, thus forming preferably a $C_{6-9}$ alkyl group. Especially preferably the substituents on the R¹ group are aryl or alkoxy which may themselves be substituted.

Thus in a particularly preferred feature R¹ represents
an optionally substituted branched $C_{5-30}$ alkyl group, preferably a $C_{6-9}$ alkyl group, comprising a straight chain $C_{4-29}$ alkyl group, preferably a $C_{5-8}$ (e.g $C_5$ or $C_6$) alkyl group, branched by substitution with one or more $C_{1-6}$ alkyl groups, preferably $C_1$ or $C_2$, wherein said site of substitution is at C2 or a higher C atom, or
an acyl or alkoxy substituted alkyl group, preferably a $C_1$ or $C_2$ alkyl group,
wherein preferably said acyl group is substituted, especially preferably substituted by one or more alkyl (e.g. $C_{1-2}$ alkyl), fluoro or nitro groups, which groups may be further substituted, and
preferably said alkoxy group is substituted by one or more further alkoxy groups, which groups may be further substituted.

In a further aspect, the present invention provides novel compounds. Thus the present invention provides compounds of formula I,

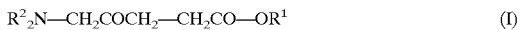

R²₂N—CH₂COCH₂—CH₂CO—OR¹ (I)

(wherein
R¹ represents
an optionally substituted branched $C_{5-30}$ alkyl group, preferably a $C_{6-9}$ alkyl group, comprising a straight chain $C_{4-29}$ alkyl group, preferably a $C_{5-8}$ (e.g $C_5$ or $C_6$) alkyl group, branched by substitution with one or more $C_{1-6}$ alkyl groups, preferably $C_1$ or $C_2$, wherein said site of substitution is at C2 or a higher C atom, or
a non-heteroaromatic aryl substituted alkyl group, preferably a $C_1$ or $C_2$ alkyl group, wherein said aryl group is substituted, especially preferably substituted by one or more alkyl (e.g. $C_{1-2}$ alkyl), fluoro or nitro groups, which groups may be further substituted, or
an alkoxy substituted alkyl group, preferably a $C_1$ or $C_2$ alkyl group, wherein said alkoxy group is substituted by a methoxy group or an alkoxy group substituted with an alkoxy group which latter group may be further substituted.
wherein said substituents are selected from hydroxy, alkoxy, acyloxy, alkoxycarbonyloxy, amino, aryl, nitro, oxo or fluoro groups,
and said alkyl group is optionally interrupted or terminated by one or more —O—, NR³—, —S— or PR³— groups;
R², each of which may be the same or different, represents a hydrogen atom or a group R¹; and
R³ represents a hydrogen or $C_{1-6}$ alkyl group).

Preferably R² are both hydrogen atoms and thus in a preferred feature, the invention provides substituted benzyl ALA esters and optionally substituted branched $C_{6-9}$ alkyl ALA esters, which may be used in methods of the invention.

Thus preferred compounds of the invention or for use in methods of the invention comprise 2-methylpentyl ALA ester, 4-methyl pentyl ALA ester, 1-ethylbutyl ALA ester, benzyl ALA ester, p-methylbenzyl ALA ester, p-nitrobenzyl ALA ester, p-[trifluoromethyl]benzyl ALA ester and p-flubrobenzyl ALA ester.

The compounds of the invention or for use in the invention may be prepared using standard processes and procedures well-known in the art for derivatization of multi-functional compounds, and especially esterification. As known in the art, such esterification of compounds may involve protection and deprotection of appropriate groups such that only the required groups: remain active and take part in the reaction under the conditions of the esterification. Thus for example the substituents of substituted alkanols used to prepare the esters may be protected during esterification. Similarly the NR²² group on the compound contributing this group to compounds of formula I may be protected during the reaction and deprotected thereafter. Such protection/deprotection procedures are well known in the art for the preparation of derivatives, and in particular, esters of well known amino-acids, see for example Mcomie in "Protective Groups in Organic Chemistry", Plenum, 1973 and T. W. Greene in "Protective Groups in Organic Chemistry", Wiley-Interscience, 1981.

In a further aspect, the present invention thus provides a process for preparing the compounds of the invention or for use in the invention, comprising forming an ester of the carboxy group of a 5-aminolevulinic acid.

The invention can thus be seen to provide a process for preparing the compounds of the invention or for use in the invention, comprising reacting a 5-aminolevulinic acid, or an esterifiable derivative thereof, with an alkanol or an ester-forming derivative thereof.

More particularly, this aspect of the invention provides a process for preparing compounds of formula I, which process comprises at least one of the following steps:

(a) reacting a compound of formula II

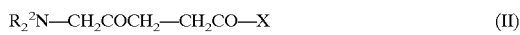
$$R_2^2N\text{—}CH_2COCH_2\text{—}CH_2CO\text{—}X \quad (II)$$

(wherein X represents a leaving group, for example a hydroxyl group, a halogen atom or alkoxy group or COX represents an acid anhydride group and $R^2$ is as hereinbefore defined)

with a compound of formula III

$$R^1\text{—}OH \quad (III)$$

(wherein $R^1$ is as hereinbefore defined); and (b) converting a compound of formula I into a pharmaceutically acceptable salt thereof.

The reaction of step (a) may conveniently be carried out in a solvent or mixture of solvents such as water, acetone, diethylether, methylformamide, tetrahydrofuran etc. at temperatures up to the boiling point of the mixture, preferably at ambient temperatures.

The conditions of the esterification reactions will depend of the alcohol used and the conditions may be chosen such that maximum yield of the ester is obtained. Since the esterification reactions are reversible equilibrium reactions, reaction conditions may be selected in such a way that maximum yield of the ester product is obtained. Such conditions may be obtained by selecting a solvent which is capable of removing the water formed in a typical esterification reaction by forming an azeotrope with water. Such solvents are exemplified by aromatic hydrocarbons or others capable of forming azeotropes with water, e.g. some chlorinated hydrocarbons such as chloroform. For the formation of the lower esters of 5-ALA the equilibrium reaction may be driven to the, ester side by using a large excess of the alcohol. With other esters the equilibrium may be driven towards the ester product by using a large excess of the acid.

Esterification reactions are well-known in the art for example, as described by Saul Patai in "The chemistry of the carboxylic acids and esters", (Ch. 11, p. 505, Interscience 1969) and Houban Weyl, (Methoden der Organische Chemie, Band E5, "Carbonsauren und carbonsaurenderivate", p. 504, Georg Thieme Verlag, 1985). The formation of derivatives of amino-acids are described in Band XI/2 of the same series, (Houben Weyl, Methoden der Organische Chemie, Band XI/2, "Stickstoffverbindungen", p. 269, Georg Thieme Verlag, 1958).

The reaction will conveniently be carried out in the presence of a catalyst, eg. an inorganic or organic acid or an acid binding agent such as a base.

The compounds used as starting materials are known from the literature, and in many cases commercially available, or may be obtained using methods known per se. ALA, for example, is available from Sigma or from Photocure, Oslo, Norway.

As mentioned above, the compounds of the invention or for use according to the invention may take the form of pharmaceutically acceptable salts. Such salts preferably are acid addition salts with physiologically acceptable organic or inorganic acids. Suitable acids include, for example, hydrochloric, hydrobromic, sulphuric, phosphoric, acetic, lactic, citric, tartaric, succinic, maleic, fumaric and ascorbic acids. Hydrophobic salts may also conveniently be produced by for example precipitation. Appropriate salts include for example acetate, bromide, chloride, citrate, hydrochloride, maleate, mesylate, nitrate, phosphate, sulphate, tartrate, oleate, stearate, tosylate, calcium, meglumine, potassium and sodium salts. Procedures for salt formation are conventional in the art.

As mentioned above, the compounds of the invention and for use according to the invention and their salts have valuable pharmacological properties, namely a photosensitizing agent which renders them useful as photochemotherapeutic agents.

A further aspect of the present invention accordingly provides a pharmaceutical composition comprising a compound as described hereinbefore, or a pharmaceutically acceptable salt thereof, together with at least one pharmaceutical carrier or excipient.

In a further aspect, there is provided a pharmaceutical composition, as described hereinbefore, for use as a medicament, e.g. in photochemotherapy or diagnosis.

In a still further aspect, there is also provided the use of a compound as described hereinbefore, or a pharmaceutically acceptable salt thereof, for the preparation of a therapeutic agent for use in photochemotherapy, and especially for the treatment of disorders or abnormalities of external or internal surfaces of the body which are responsive to photochemotherapy.

The abnormalities and disorders which may be treated according to the present invention include any malignant, pre-malignant and non-malignant abnormalities or disorders responsive to photochemotherapy eg. tumours or other growths, skin disorders such as psoriasis or actinic keratoses and acne, skin abrasions, and other diseases or infections eg. bacterial, viral or fungal infections, for example Herpes virus infections. The invention is particularly suited to the treatment of diseases, disorders or abnormalities where discrete lesions are formed to which the compositions may be directly applied (lesions is used here in a broad sense to include tumours and the like).

The internal and external body surfaces which may be treated according to the invention include the skin and all other epithelial and serosal surfaces, including for example mucosa, the linings of organs eg. the respiratory, gastrointestinal and genito-urinary tracts, and glands with ducts which empty onto such surfaces (e.g. liver, hair follicles with sebaceous glands, mammary glands, salivary glands and seminal vesicles). In addition to the skin, such surfaces include for example the lining of the vagina, the endometrium and the urothelium. Such surfaces may also include cavities formed in the body following excision of diseased or cancerous tissue eg. brain cavities following the excision of tumours such as gliomas.

Exemplary surfaces thus include: (i) skin and conjunctiva; (ii) the lining of the mouth, pharynx, oesophagus, stomach, intestines and intestinal appendages, rectum, and anal canal; (iii) the lining of the nasal passages, nasal sinuses, nasopharynx, trachea, bronchi, and bronchioles; (iv) the lining of the ureters, urinary bladder, and urethra; (v) the lining of the vagina, uterine cervix, and uterus; (vi) the parietal and visceral pleura; (vii) the lining of the peritoneal and pelvic cavities, and the surface of the organs contained within those cavities; (viii) the dura mater and meninges; (ix) any tumors in solid tissues that can be made, accessible to photoactivating light e.g. either directly, at time of surgery, or via an optical fibre inserted through a needle.

The compositions of the invention may be formulated in conventional manner with one or more physiologically acceptable carriers or excipients, according to techniques well known in the art. Where appropriate, in a preferred aspect of the invention, compounds or compositions according to the invention are sterilized, e.g. by γ-irradiation, autoclaving or heat sterilization, before or after the addition of a carrier or excipient where that is present, to provide sterile formulations.

Compositions may be administered topically, orally or systemically. Topical compositions are preferred, and include gels, creams, ointments, sprays, lotions, salves, sticks, soaps, powders, pessaries, aerosols, drops, solutions and any of the other conventional pharmaceutical forms in the art.

Ointments, gels and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops and solutions may be formulated with an aqueous or non-aqueous base also comprising one or more dispersing, solubilising or suspending agents. Aerosol sprays are conveniently delivered frompressurised packs, with the use of a suitable propellant.

Alternatively, the compositions may be provided in a form adapted for oral or parenteral administration, for example by intradermal, subcutaneous, intraperitoneal or intravenous injection. Alternative pharmaceutical forms thus include plain or coated tablets, capsules, suspensions and solutions containing, the active component optionally together with one or more inert conventional carriers and/or diluents, e.g. with corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof.

The compositions may additionally include lubricating agents, wetting agents, emulsifying agents, suspending agents, preserving agents, sweetening agents, flavouring agents, adsorption enhancers, e.g. surface penetrating agents as mentioned below, and the like. The compositions of the invention may be formulated so as to provide quick, sustained or delayed release of the active ingredient after administration to the patient by employing procedures well known in the art. Solubilizing and/or stabilizing agents may also be used, e.g. cyclodextrins (CD) α, β, γ and HP-β cyclodextrin. Compositions may be in any appropriate dosage form, for example as an emulsion or in liposomes, niosomes, microspheres, nanoparticles or the like. The compound of the invention may then be absorbed to, incorporated in or bound to these forms.

The concentration of the compounds as described hereinbefore in the compositions, depends upon the nature of the compound, the composition, mode of administration, the condition to be treated and the patient and may be varied or adjusted according to choice. Generally however, concentration ranges of 0.01 to 50%, e.g. 0.05 to 20%, e.g. 1–10% (w/w) are suitable. For therapeutic applications concentration ranges of 0.1 to 50% have been found to be suitable, e.g. 0.2 to 30% (w/w). Lower doses may be used when derivatives are prepared which are highly lipophilic, e.g. a concentration range of 0.01 to 10%, e.g. 0.02 to 1% (w/w).

Topical administration to inaccessible sites may be achieved by techniques known in the art, e.g. by the use of catheters or other appropriate drug delivery systems.

Following administration to the surface, the area treated is exposed to light to achieve the photochemotherapeutic effect. The length of time following administration, at which the light exposure takes place will depend on the nature of the composition, the condition to be treated and the form of administration. This can generally be in the order of 0.5 to 48 hours, e.g. 1 to 10 hours.

The irradiation will in general be applied at a dose level of 40 to 200 Joules/cm$^2$, for example at 100 Joules/cm$^2$.

The wavelength of light used for irradiation may be selected to achieve a more efficacious photochemotherapeutic effect. Conventionally, when porphyrins are used in photochemotherapy they are irradiated with light at about the absorption maximum of the porphyrin. Thus, for example in the case of the prior art use of ALA in photochemotherapy of skin cancer, wavelengths in the region 350–640 nm, preferably 610–635 nm were employed. However, by selecting a broad range of wavelengths for irradiation, extending beyond the absorption maximum of the porphyrin, the photosensitizing effect may be enhanced. Whilst not wishing to be bound by theory, this is thought to be due to the fact that when Pp, and other porphyrins, are exposed to light having wavelengths within its absorption spectrum, it is degraded into various photo-products including in particular photoprotoporphyrin (PPp). PPp is achlorin and has a considerable photo-sensitizing effect; its absorption spectrum stretches out to longer wavelengths beyond the wavelengths at which Pp absorbs ie. up to almost 700 nm (Pp absorbs almost no light above 650 nm). Thus in conventional photochemotherapy, the wavelengths used do not excite PPp and hence do not obtain the benefit of its additional photosensitizing effect. Irradiation with wavelengths of light in the range 500–700 nm has been found to be particularly effective. It is particularly important to include the wavelengths 630 and 690 nm.

A further aspect of the invention thus provides a method of photochemotherapeutic treatment of disorders or abnormalities of external or internal surfaces of the body, comprising administering to the affected surfaces, a composition as hereinbefore defined, and exposing said surfaces to light, preferably to light in the wavelength region 300–800 nm, for example 500–700 nm.

Methods for irradiation of different areas of the body, eg. by lamps or lasers are well known in the art (see for example Van den Bergh, Chemistry in Britain, May 1986 p. 430–439). For inaccessible regions this may conveniently belachieved using optical fibres.

The compounds of the invention or for use in the invention may be formulated and/or administered with other photosensitizing agents, for example ALA or photofrin®, or with other active components which may enhance the photochemotherapeutic effect. For example, chelating agents may beneficially be included in order to enhance accumulation of Pp; the chelation of iron by the chelating agents prevents its incorporation into Pp to form haem by the action of the enzyme ferrochelatase, thereby leading to a build-up of Pp. The photosensitizing effect is thus enhanced.

Aminopolycarboxylic acid chelating agents are particularly suitable for use in this regard, including any of the chelants described in the literature for metal detoxification or for the chelation of paramagnetic metal ions in magnetic resonance imaging contrast agents. Particular mention may be made of EDTA, CDTA (cyclohexane diamine tetraacetic acid), DTPA and DOTA and well known derivatives/analogues thereof. EDTA is preferred. To achieve the iron-chelating effect, desferrioxamine and other siderophores may also be used, e.g. in conjunction with aminopolycarboxylic acid chelating agents such as EDTA.

The chelating agent may conveniently be used at a concentration of 0.05 to 20% e.g. 0.1 to10% (w/w).

Additionally, it has been found that surface-penetration assisting agents and especially dialkylsuphoxides such as dimethylsulphoxide (DMSO) may have a beneficial effect in enhancing the photochemotherapeutic effect. This is described in detail in WO95/07077.

The surface-penetration assisting agent may be any of the skin-penetration assisting agents described in the pharmaceutical literature e.g. chelators (e.g. EDTA), surfactants (e.g. sodium dodecyl sulphate), non-surfactants, bile salts (e.g. sodium deoxycholate) and fatty acids (e.g. oleic acid). Examples of appropriate surface penetrating assisting agents include HPE-101 (available from Hisamitsu), DMSO and other dialkylsulphoxides, in particular n-decylmethylsulphoxide (NDMS), dimethylsulphacetamide, dimethylformamide (DMFA), dimethylacetamide, glycols, various pyrrolidone derivatives (Woodford et al., J. Toxicol. Cut. & Ocular Toxicology, 1986, 5: 167–177), and Azone® (Stoughton et al., Drug Dpv. Ind. Pharm. 1983, 9: 725–744), or mixtures thereof.

DMSO is however preferred due to its anti-histamine and anti-inflammatory activities and its stimulatory effect on the activity of the enzymes ALA-synthase and ALA-dehydrogenase (the enzymes which, respectively, form and condense ALA to porphobilinogen) thereby enhancing the formation of the active form, Pp.

The surface penetration agent may conveniently be provided in a concentration range of 0.2 to 50% (w/w), e.g. about 10% (w/w).

The compositions of the invention or used according to the invention may additionally be formulated and/or administered with other agents, to improve the efficacy of PDT. Furthermore, when treating tumours for example; angiogenesis inhibitors (anti-angiogenic drugs) which have been found to be useful for treating tumours (O'Reilly et al., Nature Medicine, 2, p689–692, 1996; Yamamoto et al., Anticancer Research, 14, p1–4, 1994; and Brooks et al., J. Clin. Invest., 96, p1815–1822, 1995) may be used together with compositions of the invention in PDT to further damage the vascular system of the tumour. Angiogenesis inhibitors which may be used include TNP-470 (AGM-1470, a synthetic analogue of a fungal secretion product called fumagillin; Takeda Chemical Industries Ltd., Osaka, Japan), angiostatin (Surgical Research Lab. at Children's Hospital Medical Center of Harvard Medical School) and integrin $\alpha_v\beta_3$, antagonists (e.g. monoclonal antibody to integrin $\alpha_v\beta_3$, The Scripps Research Institute, LaJolla, Calif.).

Alternatively, or additionally, immunotherapy agents (e.g. antibodies or effectors such as macrophage activating factor) or chemotherapy agents may be used to improve PDT according to the invention. Administration of these supplementary agents should be performed in terms of route, concentration and formulation, according to known methods for using these agents. These additional agents may be administered before, after or during PDT, depending on their function. For example, angiogenesis inhibitors may be added 5 to 10 days after PDT to prevent, tumour regrowth.

Other anti-cancer agents may similarly be used in combination with a composition of the invention, either as part of the formulation or as a separate treatment to be administered simultaneously, separately or sequentially.

Glucose has also been found to assist PDT when applied either topically or systemically. Although not wishing to be,bound by theory, it appears that administration of glucose results in a lowering of pH which increase the hydrophobic properties of protoporphyrins, e.g. ALA, such that they can penetrate cells more easily. When topical administration is contemplated, conveniently the formulation, e.g. a cream, may contain 0.01% to 10% glucose (w/w).

According to the condition being treated, and the nature of the composition, the compounds for use in the invention may be co-administered with such other optional agents, for example in a single composition or they may be administered sequentially or separately. Indeed, in many cases a particularly beneficial photochemotherapeutic effect may be obtained by pre-treatment with the surface-penetration assisting agent in a separate step, prior to administration of the compounds for use in the invention.

Furthermore, in some situations a pre-treatment with the surface-penetration assisting agent, followed by administration of the photochemotherapeutic agent in conjunction with the surface-penetration assisting agent may be beneficial. When a surface-penetration assisting agent is used in pre-treatment this may be used at high concentrations, e.g. up to 100% (w/w). If such a pre-treatment step is employed, the photochemotherapeutic agent may subsequently be administered up to several hours following pre-treatment eg. at an interval of 5–60 minutes following pre-treatment.

Viewed from a further aspect, the invention thus provides a product comprising a compound as described hereinbefore or a pharmaceutically acceptable salt thereof, together with at least one surface-penetration assisting agent, and optionally one or more chelating agents as a combined preparation for simultaneous, separate or sequential use in treating disorders or abnormalities of external or internal surfaces of the body which are responsive to photochemotherapy.

Alternatively viewed, this aspect of the invention also provides a kit for use in photochemotherapy of disorders or abnormalities of external or internal surfaces of the body comprising:

a) a first container containing a compound as described hereinbefore or a pharmaceutically acceptable salt thereof, b) a second container containing at least one surface penetration assisting agent; and optionally c) one or more chelating agents contained either within said first container or in a third container.

Where the surface penetration agent is applied in a separate pre-treatment step, it may be applied in higher concentration, for example up to 100% (w/w).

It will be appreciated that the method of therapy using compounds as described hereinbefore inevitably involves the fluorescence of the disorder or abnormality to be treated. Whilst the intensity of this fluorescence may be used to eliminate abnormal cells, the localization of the fluorescence may be used to visualize the size, extent and situation of the abnormality or disorder.

The abnormality or disorder thus identified or confirmed at the site of investigation may then be treated through alternative therapeutic techniques e.g. surgical or chemical treatment, or by the method of therapy of the invention by continued build up of fluorescence or through further application of compounds of the invention at the appropriate site. It will be appreciated that diagnostic techniques may require lower levels of fluorescence for visualization than used in therapeutic treatments. Thus, generally, concentration ranges of 0.2 to 30% e.g. 1–5% (w/w) are suitable. Sites, methods and modes of administration have been considered before with regard to the therapeutic uses and are applicable also to diagnostic uses described here.

The compounds of the invention or for use in the invention may also be used for in vitro diagnostic techniques, for example for examination of the cells contained in body fluids. The higher fluorescence associated with non-normal tissue may conveniently be indicative of an abnormality or disorder. This method is highly sensitive and may be used for early detection of abnormalities or disorders, for example bladder or lung carcinoma by examination of the epithelial cells in urine or sputum samples, respectively. Other useful body fluids which may be used for diagnosis in addition to urine and sputum include blood, semen, tears, spinal fluid etc. Tissue samples or preparations may also be evaluated, for example biopsy tissue or bone marrow samples. The present invention thus extends to the use of compounds of the invention, or salts thereof for diagnosis according to the aforementioned methods for photochemotherapy, and products and kits for performing said diagnosis.

A further aspect of the invention relates to a method of in vitro diagnosis, of abnormalities or disorders by assaying a sample of body fluid or tissue of a patient, said method comprising at least the following steps:

i) admixing said body fluid or tissue with a compound as described hereinbefore,
ii) exposing said mixture to light,
iii) ascertaining the level of fluorescence, and
iv) comparing the level of fluorescence to control

BRIEF DESCRIPTION OF THE DRAWINGS

The invention will now be described in more detail in the following non-limiting Examples, with reference to the drawings in which.

EXAMPLE 1

Preparation of 5-Amino-4-oxopentanoate hydrochloride Esters

General Procedure I

Figure 1:
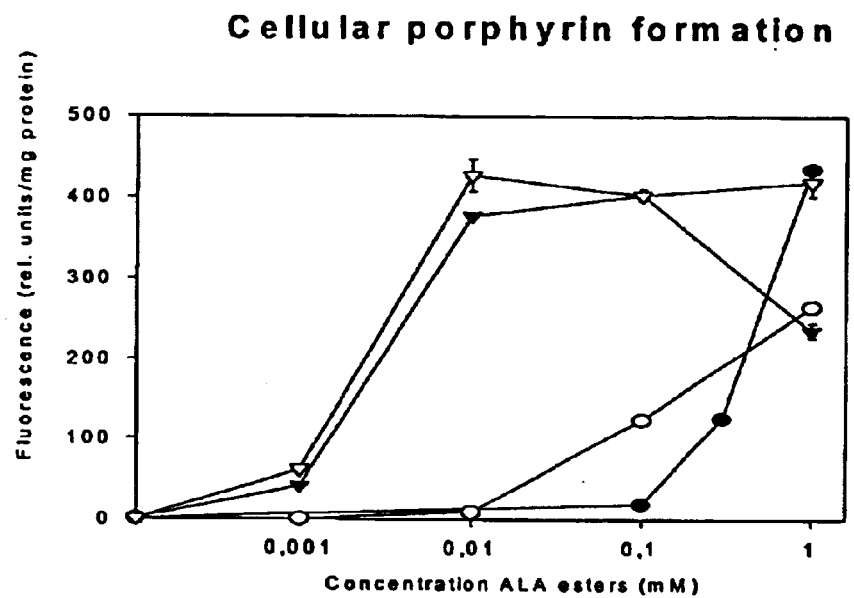
FIG. 1 shows cellular porphyrin formation induced by ALA (filled circles), 1-methylpentyl ALA ester (empty circles), p-isopropylbenzyl ALA ester (filled inverted triangles) and p-methylbenzyl ALA ester (empty inverted triangles)

Thionyl chloride (1.0 ml) was added dropwise to the stirred alcohol (6.0 ml or 5–6 g) cooled to 0° C. (bath temperature)i followed by 5-amino-4-oxopentanoic acid hydrochloride (1.0 g; 6.0 mmol) in one portion. The mixture was stirred at 70–90° C. for 1–4 hours, until a clear solution was obtained. The reaction mixture was checked by TLC [silica gel 60 on aluminum foil eluted with acetone(MeOH (3:2)]. The mixture was cooled to room temperature and added to diethyl ether (50 ml) with stirring. Filtration gave the crude ester; excess alcohol could be recovered from the filtrate.

The crude ester was purified by flash chromatography on a 150–200×25 mm silica gel 60 column eluted with acetonitrile (250 ml) and 10% MeOH in acetonitrile (500–1000 ml). The fractions containing the product were evaporated and the residue was washed with ether and dried at 30–40° C. and 0.2 mm Hg.

The following esters were prepared by this method:

Ethyl 5-amino-4-oxopentanoate hydrochloride From ethanol (6.0 ml) and 5-amino-4-oxopentanoic acid hydrochloride (1.0 g; 6.0 mmol) at 70° C. The reaction was complete after 2 h. The yield was 1.0 g (85%).

$^1$H NMR (200 MHz; DMSO-d6): δ 1.19 (3H, t, J=7.2 Hz), 2.54 (2H, t, J=6.3 Hz), 2.83 (2H, t, J=6.6 Hz), 3.96 (2H, br s), 4.05 (2H, q, J=7.0 Hz), 8.52 (3H, br s).

$^{13}$C NMR (50 MHz; DMSO-d6): δ 14.0, 27.1, 34.2, 46.4, 60.0, 171.9, 202.4.

2-Hexyl 5-amino-4-oxopentanoate hydrochloride [compound 1]

From 2-hexanol (6.0 ml) and 5-amino-4-oxopentanoic acid hydrochloride (1.0 g; 6.0 mmol) at 70° C. The reaction was complete after ca. 4 h. The yield was 1.0 g (66%).

$^1$H NMR(200 MHz; DMSO-d6): δ 0.87 (3H, t, J=6.5 Hz), 1.15 (3H, d, J=6.2 Hz), 1.25 (4H, m), 1.51 (2H, m) 2.51 (2H, t, J=6.5 Hz), 2.81 (2H, t, J=6.6 Hz), 3.95 (2H, s), 4.78 (1H, m, J=6.5 Hz), 8.47 (3H, br s).

$^{13}$C NMR (50 MHz; DMSO-d6): δ 13.6, 19.4, 21.6, 26.6, 27.0, 33.8, 34.4, 44.9, 69.6, 169.5, 200.1.

3-Hexyl 5-amino-4-oxopentanoate hydrochloride [compound 12]

From 3-hexanol (6.0 ml) and 5-amino-4-oxopentanoic acid hydrochloride (1.0 g; 6.0 mmol) at 100° C. The reaction was complete after 2 days. The yield was 0.87 g (58%) of amber oil.

$^1$H NMR (200 MHz; DMSO-d6): δ 0.83 (3H, t, J=7.4 Hz), 0.86 (3H, t, J=7.2 Hz), 1.27 (2H, m, J=7.7 Hz), 1.48 (4H, m, J=7.5 Hz), 2.54 (2H, t, J=6.3 Hz), 2.83 (2H, t, J=6.0 Hz), 3.95 (2H, s), 4.73 (1H, m, J=5.9 Hz), 8.55 (3H, br s).

$^{13}$C NMR (50 MHz; DMSO-d6): δ 9.3, 13.6, 17.8, 26.2, 26.8, 33.9, 34.8, 45.9, 73.7, 169.8, 200.1.

2-Methyl-1-pentyl 5-amino-4-oxopentanoate hydrochloride [compound 13]

From 2-methyl-1-pentanol (6.0 ml) and 5-amino-4-oxopentanoic acid hydrochloride (1.0 g; 6.0 mmol) at 70° C. The reaction was complete after 3.5 h. The yield was 1.43 g (95%).

$^1$H NMR (200 MHz, DMSO-d6): δ 0.85–0.90 (6H, m), 1.1–1.4 (4H, m), 1.74 (1H, m), 2.56 (2H, t, J=6.7 Hz), 2.84 (2H, t, J=6.6 Hz), 3.75–3.9 (2H, m), 3.95 (2H, br s), 8.52 (3H, br s).

$^{13}$C NMR (50 MHz; DMSO-d6): δ 13.9, 16.4, 19.1, 26.7, 31.3, 33.9, 34.5, 45.9, 67.9, 170.0, 200.1.

4-Methyl-1-pentyl 5-amino-4-oxopentanoate hydrochloride [compound 8]

From 4-methyl-1-pentanol (6.0 ml) and 5-amino-4-oxopentanoic acid hydrochloride (1.0 g; 6.0 mmol) at 70° C. The reaction was complete after 2 h. The yield was 1.32 g (87%).

$^1$H NMR (200 MHz; DMSO-d6): δ 0.87 (6H, d, J=6.6 Hz), 1.15–1.25 (2H, m), 1.45–1.65 (3H, m), 2.55 (2H, t, J=6.5 Hz), 2.83 (2H, t, J=6.4 Hz), 3.96 (2H, br s), 3.99 (2H, t, J=6.8 Hz), 8.53 (3H, br s).

$^{13}$C NMR (50 MHz; DMSO-d6): δ 22.0, 22.2, 25.6, 26.7, 26.8, 34.0, 45.9, 63.5, 169.9, 200.1.

3,3-Dimethyl-1-butyl 5-amino-4-oxopentanoate hydrochloride **

From 3,3-dimethyl-1-butanol (5.0 g; 49 mmol) and 5-amino-4-oxopentanoic acid hydrochloride (1.0 g; 6.0 mmol) at 70° C. The reaction was complete after 4 h. The yield was 0.91 g (60%), mp146–148°.

$^1$H NMR (200 MHz; DMSO-d6): δ 0.91 (9H, s), 1.51 (2H, t, J=7.6 Hz), 2.53 (2H, t, J=6.2 Hz), 2.83 (2H, t, J=6.2 Hz), 3.96 (2H, br s), 4.07 (2H, t, J=7.0 Hz), 8.54, (3H, br s).

$^{13}$C NMR (50 MHz; DMSO-d6): δ 27.0, 29.3, 29.34, 34.3, 46.4, 61.5, 171.9, 202.4.

Cyclohexyl 5-amino-4-oxopentanoate hydrochloride [compound 7]

From cyclohexanol (6.0 ml) and 5-amino-4-oxopentanoic acid hydrochloride (1.0 g; 6.0 mmol) at 80° C. Thionyl chloride was added at room temperature. The reaction was, complete after 3 h. The yield was 1.48 g (99%).

$^1$H NMR (200 MHz; DMSO-d6): δ 1.1–1.5 (6H, m), 1.5–1.9 (4H, m), 2.52 (2H, t, J=6.3 Hz), 2.82 (2H, t, J=6.3 Hz), 3.95 (2H, br s), 4.64 (1H, m), 8.52 (3H, br s).

$^{13}$C NMR (50 MHz; DMSO-d6): δ 22.8, 24.5, 27.1, 30.6, 33.9, 45.9, 71.2, 169.3, 200.1.

2-Phenylethyl 5-amino-4-oxopentanoate hydrochloride [compound 5]

From 2-phenylethanol (5.0 g; 41 mmol) and 5-amino-4-oxopentanoic acid hydrochloride (1.0 g; 6.0 mmol) at 70° C. The reaction was complete after 3 h. The yield was 1.43 g (88%).

$^1$H NMR (200 MHz; DMSO-d6): δ 2.50 (2H, t, J=6.4 Hz), 2.82 (2H, t, J=6.4 Hz), 2.89 (2H, t, J=7.0 Hz), 3.95 (2H, br s), 4.23 (2H, t, J=7.0 Hz), 7.1–7.4 (5H, m), 8.54 (3H, br s).

$^{13}$C NMR (50 MHz; DMSO-d6): δ 24.6, 28.0, 35.2, 47.4, 65.5, 127.2, 129.2, 129.7, 172.8, 203.3.

4-Phenyl-1-butyl 5-amino-4-oxopentanoate hydrochloride [compound 14]

From 4-phenyl-1-butanol (5.0 g; 33 mmol) and 5-amino-4-oxopentanoic acid hydrochloride (1.0 g; 6.0 mmol) at 70° C. The reaction was complete after 29 h. The yield was 1.22 g (68%).

$^1$H NMR (200 MHz; DMSO-d6): δ 1.60 (4H, br s), 2.5–2.6 (4H, m), 2.84 (2H, t, J=6.4 Hz), 3.97 (2H, br s), 4.0 (2H, m), 7.15–7.35 (5H, m), 8.56 (3H, br s).

$^{13}$C NMR (50 MHz; DMSO-d6): δ 27.0, 27.2, 27.6, 34.3, 34.6, 46.4, 63.8, 125.6, 128.2, 141.8, 171.9, 202.4.

2-Methoxyethyl 5-amino-4-oxopentanoate hydrochloride **

From 2-methoxyethanol (5.0 g; 66 mmol) and 5-amino-4-oxopentanoic acid hydrochloride (1.0 g; 6.0 mmol) at 70° C. The reaction was complete after 1 h. The yield was 1.25 g (93%) of yellowish oil.

$^1$H NMR (200 MHz; DMSO-d6): δ 2.57 (2H, t, J=6.2 Hz), 2.83 (2H, t, J=6.2 Hz), 3.27 (3H, s), 3.54 (5H, br s), 3.95 (2H, br s), 4.12 (2H, br s), 8.52 (3H, br s).

$^{13}$C NMR (50 MHz; DMSO-d6): δ 27.1, 34.3, 46.5, 58.0, 63.2, 69.6, 172.0, 202.5.

3,6-Dioxa-1-octyl 5-amino-4-oxopentanoate hydrochloride **

From diethylene glycol monoethyl ether (5.0 g; 37 mmol) and 5-amino-4-oxopentanoic acid hydrochloride (1.0 g; 6.0 mmol) at 70° C. The reaction was complete after 4 h. The yield was 0.90 g (53%) of light tan solid.

$^1$H NMR (200 MHz; DMSO-d6): δ 1.10 (3H, t, J=7.0 Hz), 2.58 (2H, t, J=6.0 Hz), 3.35–3.65 (8H, m), 3.96 (2, br s), 4.13 (2H, t, J=4.2 Hz), 8.52 (3H, br s).

$^{13}$C NMR (50 MHz; DMSO-d6): δ 15.0, 27.1, 34.3, 46.5, 63.4, 65.5, 68.1, 69.1, 69.8, 172.0, 202.5.

3,6,9-Trioxa-1-decyl 5-amino-4-oxopentanoate hydrochloride **

From triethylene glycol monomethyl ether (5.0 g; 30 mmol) and 5-amino-4-oxopentanoic acid hydrochloride (1.0 g; 6.0 mmol) at 70° C. The reaction was complete after 20 h. The yield!was 1.19 g (63%) brownish oil.

$^1$H NMR (200 MHz; DMSO-d6): δ 2.58 (2H, t, J=6.2 Hz), 2.84 (2H, t, J=6.4 Hz), 3.25 (3H, s), 3.4–3.65 (10H, m), 3.96 (2H, br s), 4.13 (2H, m), 8.49 (3H, br s).

$^{13}$C NMR (50 MHz; DMSO-d6): δ 27.1, 34.3, 46.5, 58.0, 63.4, 68.1, 69.5, 69.6, 69.7, 71.2, 171.9, 202.5.

General Procedure II

A mixture of the alcohol (5.0 g) and 5-amino-4-oxopentanoic acid hydrochloride (1.0 g; 6.0 mmol) was heated to 90° C. (up to 135° if necessary to melt the alcohol) and 12 M hydrochloric acid (0.1 ml) was added. Heating was continued until a clear solution was obtained (up to 5 days). Work-up as in the previous, procedure.

The following esters were prepared by this method:

Benzyl 5-amino-4-oxopentanoate hydrochloride [compound 4]

From benzyl alcohol (50 ml) and 5-amino-4-oxopentanoic acid hydrochloride (10.0 g; 60 mmol). After 23 h at 90°, excess benzyl alcohol was distilled off at 90° (bath temperature) and 0.33 mm Hg. The yield was 8.1 g (53%) of tan powder.

$^1$H NMR (200 MHz; DMSO-d6): δ 2.63 (2H, t, J=6.5 Hz), 2.87 (2H, t, J=6.5 Hz), 3.98 (2H, br s), 5.11 (2H, s), 7.3–7.4 (5H, br s), 8.52 (3H, br s).

$^{13}$H NMR (50 MHz; DMSO-d6): δ 26.7, 33.8, 45.9, 64.8, 126.3, 126.4, 12:6.8, 134.4, 169.8, 200.1.

4-Nitrobenzyl 5-amino-4-oxopentanoate hydrochloride [compound 11]

From 4-nitrobenzyl alcohol (5.0 g; 33 mmol) and 5-amino-4-oxopentanoic acid hydrochloride (1.0 g; 6.0 mmol). The reaction was complete after 15 min at 135° C. The yield was 0.95 g (52%).

$^1$H NMR (200 MHz; DMSO-d6): δ 2.72 (2H, t, J=5.8 Hz), 2.91 (2H, t, J=6.2 Hz), 4.02 (2H, br s), 5.28 (2H, s), 7.67 (2H, d, J=8.0 Hz), 8.25 (2H, d, J=9.1 Hz), 8.58 (3H, br s).

$^{13}$C NMR (50 MHz; DMSO-d6): δ 27.1, 34.3, 46.5, 64.4, 123.5, 128.3, 143.9, 146.9, 171.8, 202.5.

4-Fluorobenzyl 5-amino-4-oxopentanoate hydrochloride [compound 15]

From 4-fluorobenzyl alcohol (5.0 g; 40 mmol) and 5-amino-4-oxopentanoic acid hydrochloride (1.0 g; 6.0 mmol). The reaction was complete after 3 h at 90° C. The yield was 1.02 g (62%).

$^1$H NMR (200 MHz; DMSO-d6): δ 2.63 (2H, t, J=6.4 Hz), 2.88 (2H, t, J=6.6 Hz), 3.99 (2H, br s), 5.10 (2H, s), 7.22 (2H, t, J=8.8 Hz), 7.45 (2H, d, J=8.0 Hz), 8.57 (3H, br s).

$^{13}$C NMR (50 MHz; DMSO-d6): δ 27.1, 34.3, 46.5, 64.9, 115.0, 115.4, 130.1, 130.2, 132.2, 132.3, 159.3, 164.2, 171.8, 202.4.

4-Methylbenzyl 5-amino-4-oxopentanoate hydrochloride [compound 3]

From 4-methylbenzyl alcohol (5.0 g; 41 mmol) and 5-amino-4-oxopentanoic acid hydrochloride (1.0 g; 6.0 mmol). The reaction was complete after 2 days. The yield was 0.84 g (52%).

$^1$H NMR (200 MHz; DMSO-d6): δ 2.30 (3H, s), 2.60 (2H, t, J=6.4 Hz), 2.86 (2H, t, J=6.2 Hz), 3.96 (2H, br s), 5.05 (2H, s), 7.1–7.3 (4H, m), 8.55 (3H, br s).

$^{13}$C NMR (50 MHz; DMSO-d6): δ 21.7, 28.1, 35.2, 47.4, 66.4, 128.9, 129.8, 133.9, 138.2, 172.8, 203.4.

4-Isopropylbenzyl 5-amino-4-oxopentanoate hydrochloride [compound 21]

From 4-isopropylbenzyl alcohol (5.0 ml) and 5-amino-4-oxopentanoic acid hydrochloride (1.0 g; 6.0 mmol). The reaction was complete after 2 days. The yield was 1.0 g (56%).

$^1$H NMR (200 MHz; DMSO-d6): δ 1.19 (6H, d, J=6.6 Hz), 2.61 (2H, t, J=6.4 Hz), 2.84 (1H, m), 2.88 (2H, t, J=6.8 Hz), 3.98 (2H, br s), 5.06 (2H, s), 7.2–7.4 (4H, m), 8.56 (3H, br s).

$^{13}$C NMR (50 MHz; DMSO-d6): δ 23.7, 27.1, 33.1, 34.3, 46.4, 65.5, 126.2, 128.0, 133.3, 148.2, 171.8, 202.6.

4-t-Butylbenzyl 5-amino-4-oxopentanoate hydrochloride [compound 10]

From 4-t-butylbenzyl alcohol (5.0 g; 30 mmol) and 5-amino-4-oxopentanoic acid hydrochloride (1.0 g; 6.0 mmol). The reaction was complete after 2 days. The yield was 0.84 9 (52%).

$^1$H NMR (200 MHz; DMSO-d6): δ 1.27 (9H, s), 2.61 (2H, t, J=6.4 Hz), 2.87 (2H, t, J=6.6 Hz), 3.98 (2H, br s), 5.06 (2H, s), 7.29 (2H, d, J=8.4 Hz), 7.39 (2H, d, J=8.4 Hz), 8.55 (3H, br 5).

$^{13}$C NMR (50 MHz; DMSO-d6): δ 21.1, 31.0, 34.16, 34.26, 46.4, 65.4, 125.0, 127.7, 133.0, 150.4, 171.8, 202.4.

4-(Trifluoromethyl)benzyl 5-amino-4-oxopentanoate hydrochloride [compound 9]

From 4-(trifluoromethyl)benzyl alcohol (4.9 g; 28 mmol) and 5-amino-4-oxopentanoic acid hydrochloride (1.0 g; 6.0 mmol). The reaction was complete after 2 h. The yield was 1.24 g (64%).

$^1$H NMR (200 MHz; DMSO-d6): δ 2.69 (2H, t, J=6.2 Hz), 2.92 (2H, t, J=6.4 Hz), 4.00 (2H, br s), 5.23 (2H, s), 7.62 (2H, d, J=8.2 Hz), 7.75 (2H, d, J=8.2 Hz), 8.58 (3H, br s).

$^{13}$C NMR (50 MHz; DMSO-d6): δ 27.1, 34.4, 46.5, 64.7, 121.4, 125.2, 125.3, 125.4, 126.9, 128.2, 140.9, 171.8, 202.5.

EXAMPLE 2

Measurement of Porphyrin Formation in Cell Culture in vitro

Methods

The following compounds were tested relative to ALA:

1. 1-methylpentyl ALA ester
2. p-isopropylbenzyl ALA ester
3. p-methylbenzyl ALA ester
4. benzyl ALA ester
5. 2-phenylethyl ALA ester
6. hexyl ALA ester
7. cyclohexyl ALA ester
8. 4-methylpentyl ALA ester
9. p-[tri-flutoromethyl]benzyl ALA ester
10. p-[t-butyl]benzyl ALA ester
11. p-nitrobenlzyl ALA ester The test compounds were dissolved in DMSO to a concentration of 100 mM (stock solution). Appropriate concentrations were obtained by dilution of the stock solutions with phosphate-buffered saline (PBS) or culture medium.

Cell Cultivation

WiDr cells, derived form a primary adenocarcinoma of the rectosigmoid colon, were subcultured in RPMI 1640 medium (Gibco) containing 10% fetal calf serum, 100 U/ml penicillin, 100 μg/ml streptomycin and 1% glutamine. Cells were split 1:100 twice a week, and maintained at 37° C. and 5% CO2 in a humid environment.

Treatment Conditions $5\times10^5$ WiDr cells in 2 ml of RPMI medium as described in the previous paragraph were added to each well in 6-well plastic tissue-culture plates (Nunc) and left for 48 hr at 37° C. and 5% $CO_2$ in a humid environment for proper attachment to the substratum. The cells were then washed twice with RPMI 1640-medium without serum, followed by the addition to the wells of the appropriate dilutions of the test compounds in 2 ml of fresh culture medium to final concentrations of 0.001, 0.01, 0.1 and 1 mM in duplicate. The cells were incubated at 37° C. for four hours.

Measurement of Cellular Porphyrin Contents

After treatment as described in the paragraph "treatment conditions" the cells were washed twice with PBS and brought into a solution of 1M $HClO_4$ in 50% MeOH by scraping the cells off the substratum by means of a Costar cell scraper. Cell debris was removed by centrifugation. The porphyrin content of each sample was determined fluorometrically using a Perkin Elmer LS50B spectrofluorimeter (excitation at 407 nm, emission was measured at 606 nm using a long pass cut-off filter (530 nm) on the emission side). The fluorescence in each sample was calculated relative to the protein content in control cells as measured by the Bradford method.

Results

The results are shown in FIGS. 1 to 4 for test compounds 1–3, 4 & 5, 6–8 and 9–11, respectively.

It can be seen from FIG. 1 that steep dose-response curves were found for both the p-methylbenzyl- and the p-isopropylbenzyl esters. These esters were equally efficient in inducing cellular porphyrin synthesis and approximately 200 times more potent than ALA. The curve for the 1-methylpentyl ester increased slowly with increasing ester concentrations. The 1-methylpentyl ester at low concentrations was only slightly better than ALA in inducing porphyrin formation.

Figure 2:
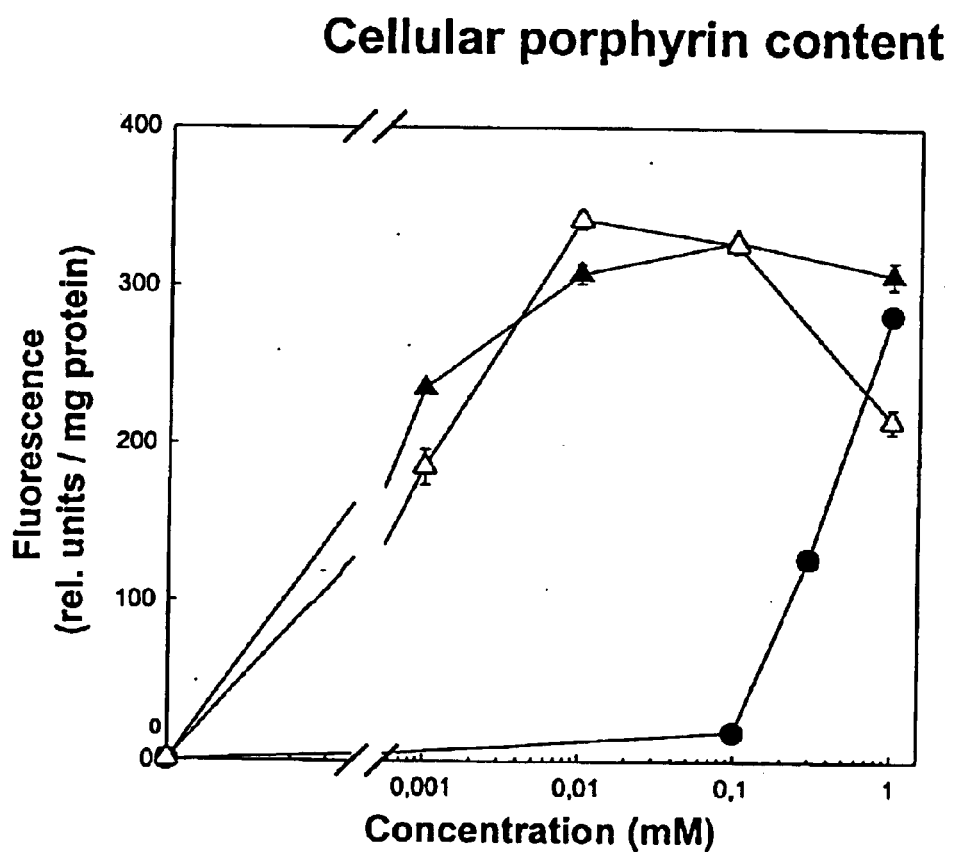
FIG. 2 shows cellular porphyrin formation induced by ALA (filled circles), benzyl ALA ester (filled triangles) and2-phenylethyl ALA ester (empty triangles), bars indicate standard deviation.

From FIG. 2 it can be seen that both the benzyl and 2-phenylethyl esters were considerably more efficient than ALA in inducing cellular porphyrin synthesis. In fact, the porphyrin formation induced by 0.001 mM benzyl ester equals that obtained with 0.6 mM ALA. Similarly, it can be seen that the fluorescence following the addition of 0.001 mM 2-phenylethyl ester corresponds to that induced by 0.4 mM ALA.

Figure 3:
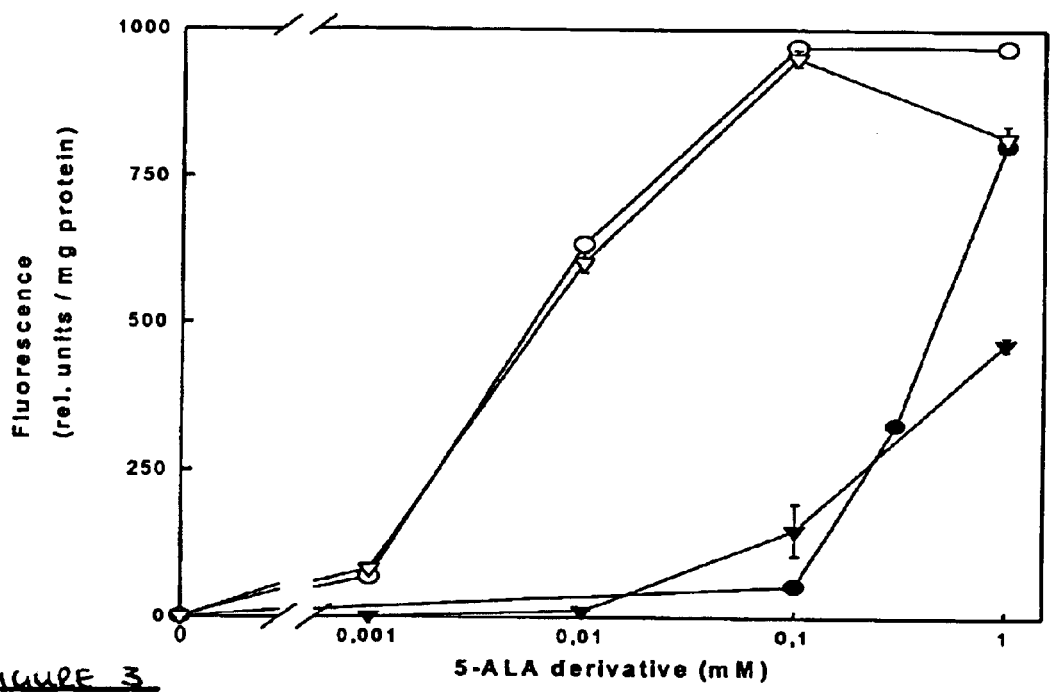
FIG. 3 shows cellular porphyrin formation induced by ALA (filled circles), hexyl ALA ester (empty circles), cyclohexyl ALA ester (filled inverted triangles) and 14-methylpentyl ALA ester (empty inverted triangles), bars indicate standard error.

FIG. 3 shows that both the hexyl- and the 4-methylpentyl esters were equally efficient. It can also be seen from the Figure that the abilities of these esters to induce cellular porphyrin formation were approximately 100 times higher than that of ALA. The cyclohexyl ester was, at low concentrations, only slightly more efficient than ALA in inducing porphyrin formation. At higher concentrations, the cyclohexyl ester was less effective than ALA.

Figure 4:
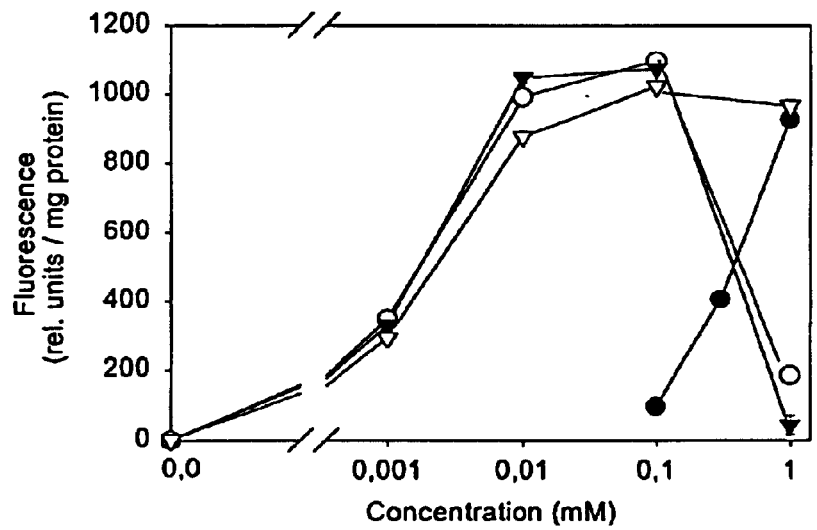
FIG. 4 shows cellular porphyrin formation induced by ALA (filled circles), p-[tri-fluoromethyl]benzyl ALA ester (empty circles); p-[(t-butyl]benzyl ALA ester (filled inverted triangles) and p-nitrobenzyl ALA ester (empty inverted triangles)

It can be seen from the FIG. 4 that the p-[tri-fluoromethyl] benzyl, p-[t-butyl]benzyl and p-nitrobenzyl esters were approximately 200 times better than ALA in inducing porphyrin formation.

The results may be summarized as follows:

| COMPOUND (IE. ESTER SIDE CHAIN) [COMPOUND NO.] | POTENCY* |
|---|---|
| ALA | 1 |
| 1-methylpentyl [1] | 3 |
| 4-methylpentyl [8] | 100 |
| 2-phenylethyl [5] | 500 |
| benzyl [4] | 100–600 |
| hexyl [6] | 100 |
| p-isopropylbenzyl [2] | 200 |
| p-methylbenzyl [3] | 200 |
| cyclohexyl [7] | 1 |
| p-nitrobenzyl [11] | 200 |
| p-[trifluoromethyl]benzyl [9] | 200 |
| p-[t-butyl]benzyl [10] | 200 |

*Relative ability to induce porphyrin formation

EXAMPLE 3

Porphyrin Formation After Topical Application Onto Murine Skin

Methods

The following compounds were tested relative to ALA (including compounds 1 to 11 tested in Example 2):

1. 1-methylpentyl ALA ester
2. p-isopropylbenzyl ALA ester
3. p-methylbenzyl ALA ester
4. benzyl ALA ester
5. 2-phenylethyl ALA ester
6. hexyl ALA ester
7. cyclohexyl ALA ester
8. 4-methylpentyl ALA ester
9. p-[tri-fluoromethyl]benzyl ALA ester
10. p-[t-butyl]benzyl ALA ester
11. p-nitrobenzyl ALA ester
12. 1-ethylbutyl ALA ester
13. 2-methylpentyl ALA ester
14. 4-phenyl butyl ALA ester
15. p-fluorobenzyl ALA ester
16. t-butyl ALA ester Methods The test compounds were formulated in Unguentum Merck (cream base available from Merck, consisting of silicon dioxide, paraffin liq., vaseline, album, cetostearol, polysorbat. 40, glycerol monostearate, Miglyol®812 (a mixture of plant fatty acids), polypropyleneglycol, and purified water) to the desired concentration. Concentrations are given as % (w/w) calculated as hydrochlorides. The formulations were prepared the day before the experiment commenced and stored in the refrigerator until the day of use. Female Balb/c athymic nude mice, weighing about 22 g, obtained from the Department of Laboratory Animals, The Norwegian Radium Hospital (Montebello, Oslo, Norway) were used in the studies.

Three mice per group was used. Each mouse received 0.05–0.1 g of formulation topically applied at the right flank of the body, evenly distributed and covered with a dressing (Opsite Flexigrid; Smith and Nephew Medical Ltd., Hull, England). The fiber point measuring device consisted of a bundle of optical fibers connected to a spectrofluorimeter which produced the excitation light of 407 nm. The excitation light, which is able to penetrate 0.1–0.5 mm into the tissue, was led through half of the fibers to the mouse skin. The resulting emission fluorescence spectrum (550–750) nm was collected and led through the remaining fibers into a photomultiplier for quantification.

After application of the cream formulation, the fluorescence spectrum from porphyrins in the skin was measured by the fiber-optical method at different intervals of time after administration.

The fluorescence intensity varied from experiment to experiment. Therefore 1% (w/w) hexyl 5-aminolevulinate-HCl was included in each experiment as an internal control.

Results

Figure 5:
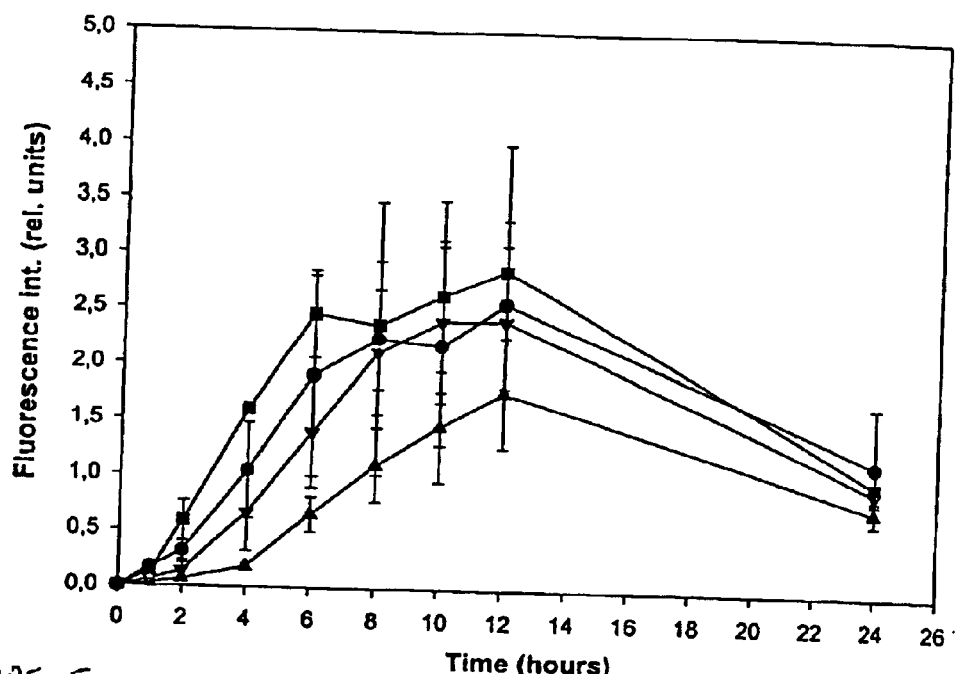
FIG. 5 shows skin fluorescence after topical application of hexyl ALA ester (filled squares), 1-methylpentyl ALA ester (filled triangles), 1-ethylbutyl ALA ester (filled inverted triangles) and 2-methylpentyl ALA ester (filled circles), bars indicate standard error.
Figure 6:
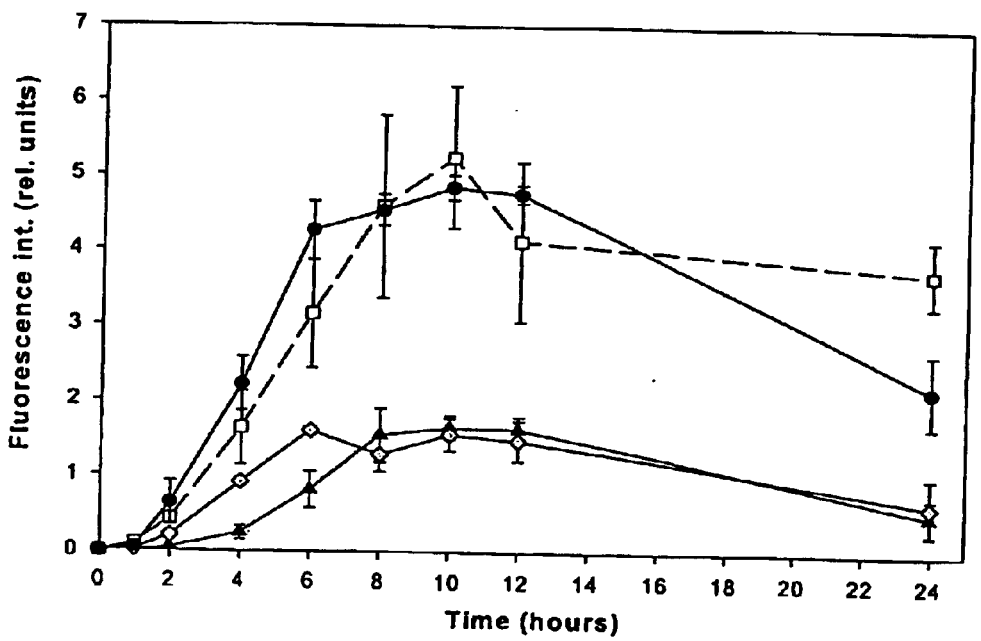
FIG. 6 shows skin fluorescence after topical application of hexyl ALA ester (empty squares), cyclohexyl ALA ester (filled triangles), 2-phenylethyl ALA ester (shaded squares) and 4-methylpentyl ALA ester (filled circles), bars indicate standard error.
Figure 7:
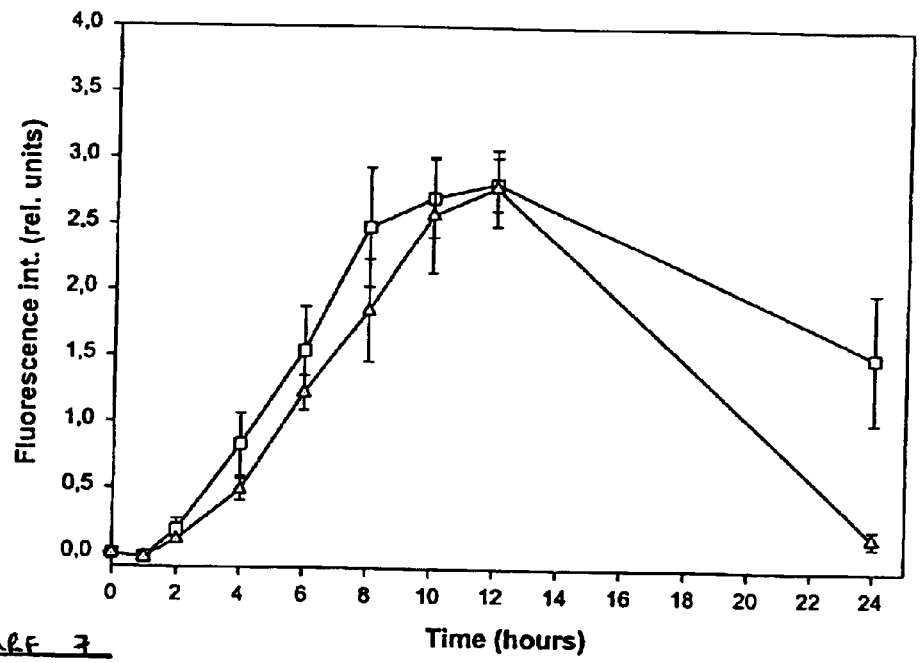
FIG. 7 shows skin fluorescence after topical application of hexyl ALA ester (empty squares) and p-methylbenzyl ALA ester (shaded triangles), bars indicate standard error.
Figure 8:
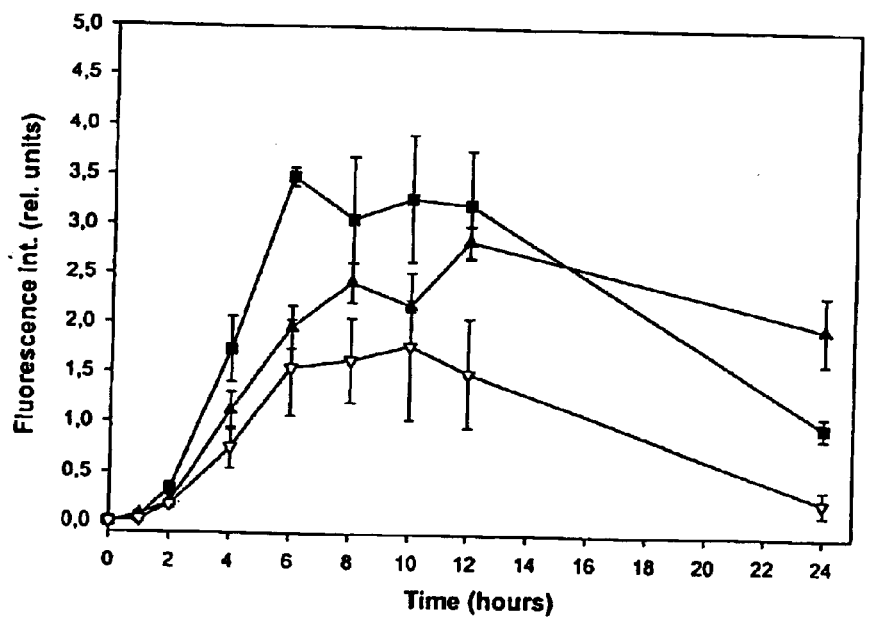
FIG. 8 shows skin fluorescence after topical application of hexyl ALA ester (filled squares), p-(isopropyl)benzyl ALA ester (filled triangles) and 4-phenylbutyl ALA ester (shaded inverted triangles), bars indicate standard error.
Figure 9:
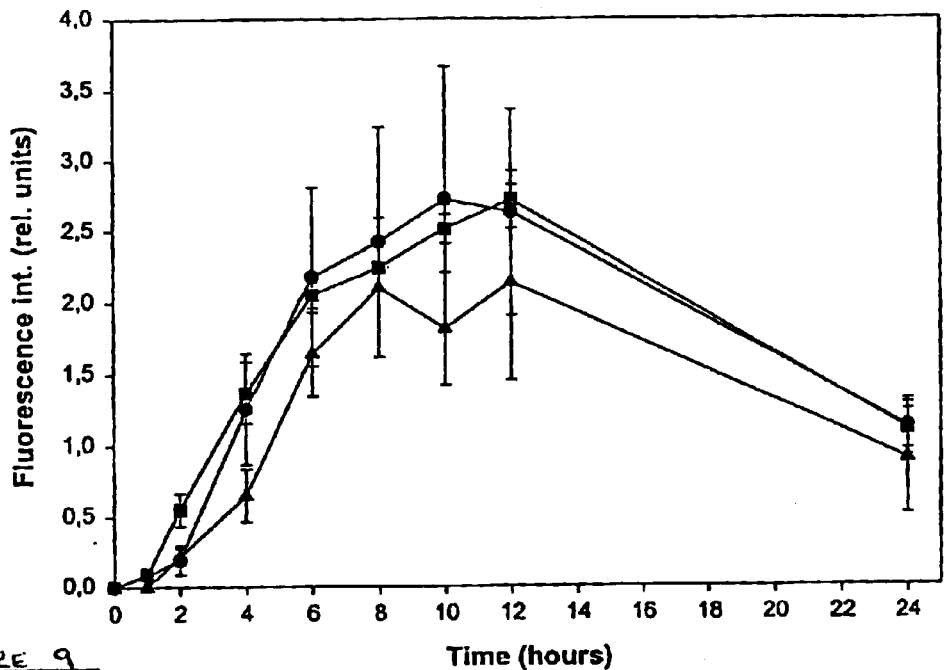
FIG. 9 shows skin fluorescence after topical application of hexyl ALA ester (filled squares), p-fluorobenzyl ALA ester (filled triangles) and p-nitrobenzyl ALA ester (filled circles), bars indicate standard error.
Figure 10:
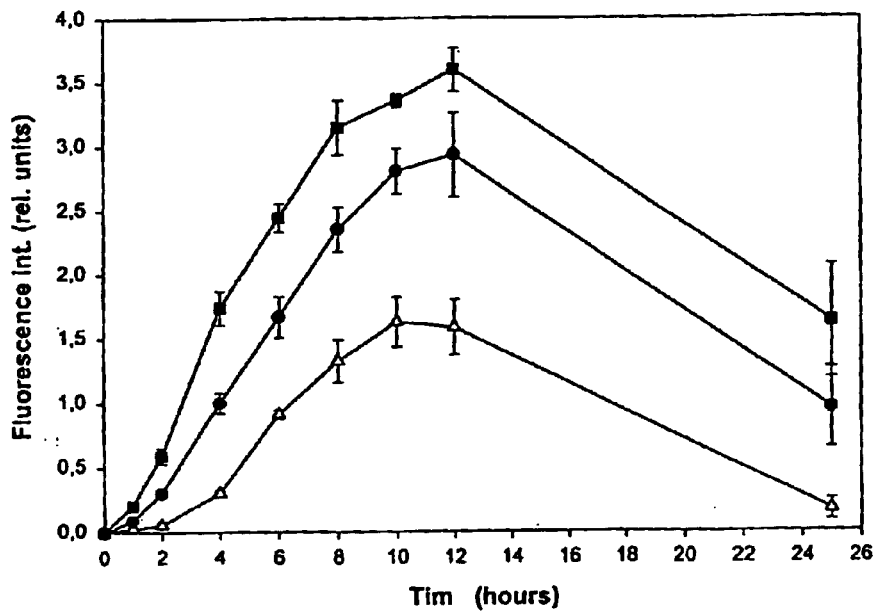
FIG. 10 shows skin fluorescence after topical application of hexyl ALA ester (filled squares), p(t-butyl)benzyl ALA ester (shaded triangles) and p-[tri-fluoromethyl]benzyl ALA ester (filled circles), bars indicate standard error.
Figure 11:
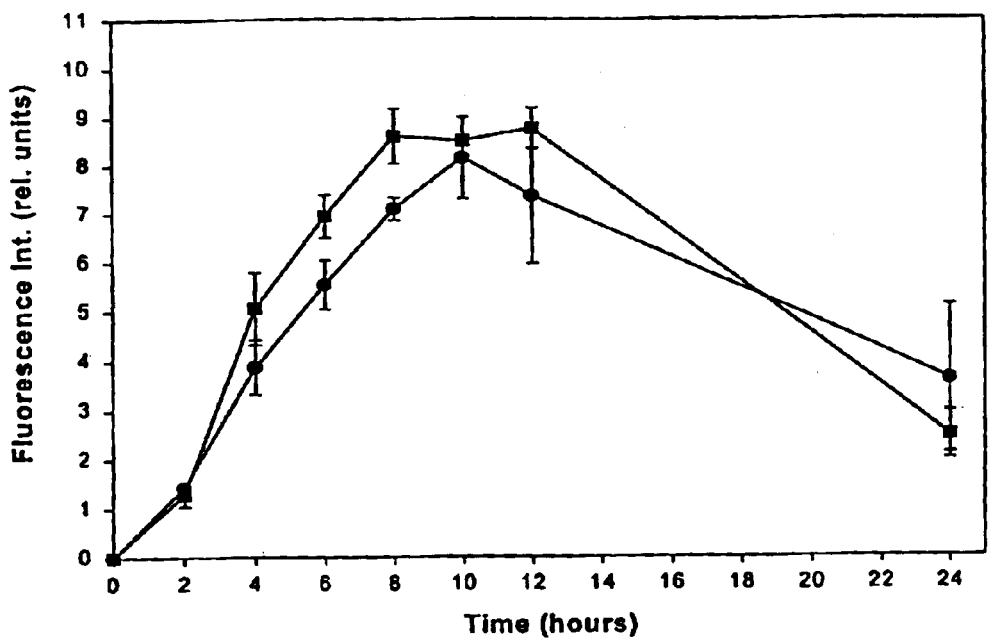
FIG. 11 shows skin fluorescence after topical application of hexyl ALA ester (filled squares) and benzyl ALA ester (filled circles), bars indicate standard error.
Figure 12:
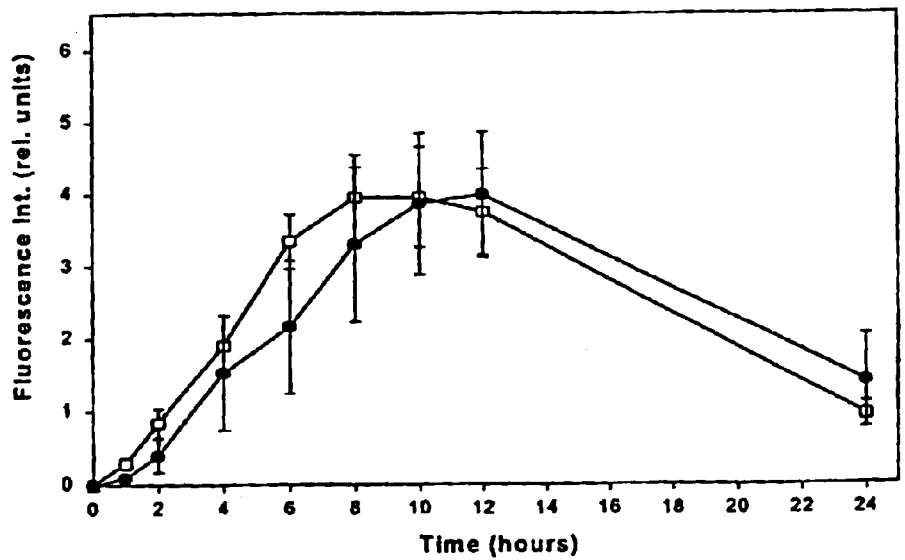
FIG. 12 shows skin fluorescence after topical application of 1% hexyl ALA ester (open squares) and 10% t-butyl ALA ester (filled circles), bars indicate standard error.

The results are shown in FIGS. 5 to 12 for the following test compounds: FIG. 5—compounds 1, 6, 12 and 13; FIG. 6—compounds 5–8; FIG. 7—compounds 3 and 6; FIG. 8—compounds 2, 6 and 14; FIG. 9—compounds 6, 11 and 15; FIG. 10—compounds 6, 9 and 10; FIG. 11—compounds 4 and 6; FIG. 12—compounds 6 and 12; All compounds were used at 1% except in FIG. 12 where t-butyl ALA ester was used at 10%.

It can be seen from the FIG. 5 that the hexyl, 1-methylpentyl, 1-ethylbutyl and 2-methylpentyl esters all gave porphyrin formation. Furthermore, the hexyl ester gave the highest fluorescence followed by the 2-methylpentyl and the 1-ethylbutyl esters. The 1-methylpentyl ester gave intermediate fluorescence levels in this study.

FIG. 6 shows that the hexyl ester and the 4-methylpentyl ester result in high fluorescence levels whereas the cyclohexyl and the 2-phenylethyl esters gave low levels of fluorescence.

FIG. 7 shows that both hexyl and p-methylbenzyl ALA esters gave high and similar levels of fluorescence.

It is evident from FIG. 8 that the p-isopropyl-benzyl 5-aminolevulinate resulted in intermediate levels of fluorescence whereas the 4-phenyl-butyl 5-aminolevulinate gave only low fluorescence levels. It is interesting in this regard that an analogue to the latter substance (the 2-phenyl-ethyl 5-aminolevulinate) also gave relatively modest fluorescence levels values (FIG. 6). This shows that when the benzyl 5-aminolevulinate (FIG. 11) is "extended" with one or more methylene ($-CH_2-$) groups between the benzyl and ALA, a reduced capability to induce porphyrin formation results.

FIG. 9 shows that the p-nitrobenzyl- and hexyl esters both gave high levels of fluorescence. Slightly lower levels were obtained with the p-fluorobenzyl ester.

FIG. 10 shows that high porphyrin formation (as indicated by high fluorescence levels) was obtained with the hexyl- and the p-[tri-fluoromethyl]benzyl esters. Intermediate fluorescence levels was obtained with the p(tert-butyl)benzyl ester. This is possibly due to the rather bulky ester group.

It is evident from FIG. 11 that high levels of fluorescence were obtained with both the hexyl- and the benzyl esters.

It is seen from FIG. 12 that high fluorescence values were obtained for the 1% hexyl ester and from the 10% formulation of the t-butyl ester. Thus, the t-butyl ester is not as effective as the hexyl ester in inducing porphyrin formation in the skin.

The results may be summarized as follows:

| COMPOUND (IE. ESTER SIDE CHAIN) [COMPOUND NO.] | FLUORESCENCE LEVEL | | |
|---|---|---|---|
| | LOW | INT. | HIGH |
| 1-methylpentyl [1] | X | | |
| 2-methylpentyl [13] | | | X |
| 4-methylpentyl [8] | | | X |
| 1-ethylbutyl [12] | | | X |
| hexyl [6] | | | X |
| t-butyl [16] | | X | |
| 2-phenylethyl [5] | X | | |
| 4-phenylbutyl [14] | X | | |
| benzyl [4] | | | X |
| p-isopropylbenzyl [2] | | X | |
| p-methylbenzyl [3] | | | X |
| p-nitrobenzyl [11] | | | X |
| p-[trifluoromethyl]benzyl [9] | | | X |
| p-[t-butyl]benzyl [10] | | X | |
| p-fluorobenzyl [15] | | | X |
| cyclohexyl [7] | X | | |

What is claimed is:

1. A compound of formula I, $$R^2{}_2N-CH_2COCH_2-CH_2CO-OR^1 \qquad (I)$$

wherein $R^1$ represents (a) an optionally substituted branched $C_{6-30}$ alkyl group, comprising a straight chain $C_{4-29}$ alkyl group, branched by substitution with one or more $C_{1-6}$ alkyl groups, wherein said site of substitution is at C2 or a higher C atom, or (b) a non-heteroaromatic aryl substituted alkyl group, wherein said aryl group is substituted, or (c) an alkoxy substituted alkyl group, wherein said alkoxy group is substituted by a methoxy group or an alkoxy group substituted with an alkoxy group, wherein in (a) and (b) said substituents are selected from hydroxy, alkoxy, acyloxy, alkoxycarbonyloxy, amino, aryl, nitro, oxo or fluoro groups, and said alkyl group is optionally interrupted or terminated by one or more —O—, $NR^3$—, —S— or $PR^3$— groups; $R^2$, each of which may be the same or different, represents a hydrogen atom or a group $R^1$, wherein $R^1$ represents (a) an optionally substituted branched $C_{5-30}$ alkyl group, comprising a straight chain $C_{4-29}$ alkyl group, branched by substitution with one or more $C_{1-6}$ alkyl groups, wherein said site of substitution is at C2 or a higher C atom, or (b) a non-heteroaromatic aryl substituted alkyl group, wherein said aryl group is substituted, or (c) an alkoxy substituted alkyl group, wherein said alkoxy group is substituted by a methoxy group or an alkoxy group substituted with an alkoxy group, wherein in (a) and (b) said substituents are selected from hydroxy, alkoxy, acyloxy, alkoxycarbonyloxy, amino, aryl, nitro, oxo or fluoro groups, and said alkyl group is optionally interrupted or terminated by one or more —O—, $NR^3$—, —S— or $PR^3$— groups; and $R^3$ represents a hydrogen or $C_{1-6}$ alkyl group).

2. The compound of claim 1 wherein $R^2$ are both hydrogen atoms.

3. The compound of claim 1 wherein the compound is 2-methylpentyl ALA ester, 4-methyl pentyl ALA ester, 1-ethylbutyl ALA ester, substituted-benzyl ALA ester, p-methylbenzyl ALA ester, p-nitrobenzyl ALA ester, p-[trifluoromethyl]benzyl ALA ester or p-fluorobenzyl ALA ester.

4. A pharmaceutical composition comprising a compound of claim 1, or a pharmaceutically acceptable salt thereof, and at least one pharmaceutical carrier or excipient.

5. A method of diagnosis or photochemotherapeutic treatment of disorders or abnormalities of external or internal surfaces of the body, comprising administering to the affected surfaces, a composition as defined in claim 4, and exposing said surfaces to light.

6. The method of claim 5 wherein the light is in the wavelength region 300–800 nm.

7. A product comprising a compound of claim 1, or a pharmaceutically acceptable salt thereof, at least one surface-penetration assisting agent, and optionally one or more chelating agents as a combined preparation for simultaneous, separate or sequential use in treating disorders or abnormalities of external or internal surfaces of the body which are responsive to photochemotherapy.

8. A kit for use in photochemotherapy of disorders or abnormalities of external or internal surfaces of the body comprising:

a) a first container containing a compound of claim 1, or a pharmaceutically acceptable salt thereof, b) a second container containing at least one surface penetration assisting agent; and optionally c) one or more chelating agents contained either within said first container or in a third container.

9. A method of in vitro diagnosis, of abnormalities or disorders by assaying a sample of body fluid or tissue of a patient, said method comprising at least the following steps:

i) admixing said body fluid or tissue with a compound of claim 1, ii) exposing said mixture to light, iii) ascertaining the level of fluorescence, and iv) comparing the level of fluorescence to control levels.

10. The compound of claim 1, wherein the optionally substituted branched $C_{6-30}$ alkyl group is a $C_{6-9}$ alkyl group.

11. The compound of claim 1, wherein the straight chain $C_{4-29}$ alkyl group is a $C_{5-8}$ alkyl group.

12. The compound of claim 1, wherein the one or more $C_{1-6}$ alkyl groups is a $C_1$ or $C_2$.

13. The compound of claim 1, wherein the non-heteroaromatic aryl substituted alkyl group is a $C_1$ or $C_2$ alkyl group.

14. The compound of claim 1, wherein the non-heteroaromatic aryl group is substituted with one or more alkyl, fluoro or nitro groups.

15. The compound of claim 14, wherein the one or more alkyl groups are substituted.

16. The compound of claim 1, wherein the alkoxy substituted alkyl group is a $C_1$ or $C_2$ alkyl group.

17. The compound of claim 1, wherein the alkoxy group substituent is substituted.

18. The pharmaceutical composition of claim 4, wherein $R^2$ in said compound are both hydrogen atoms.

19. The pharmaceutical composition of claim 18, wherein the compound is 2-methylpentyl ALA ester, 4-methyl pentyl ALA ester, 1-ethylbutyl ALA ester, substituted benzyl ALA ester, p-methylbenzyl ALA ester, p-nitrobenzyl ALA ester, p-[trifluoromethyl]benzyl ALA ester or p-fluorobenzyl ALA ester.

20. The product of claim 7, wherein $R^2$ in said compound are both hydrogen atoms.

21. The product of claim 20, wherein the compound is 2-methylpentyl ALA ester, 4-methyl pentyl ALA ester, 1-ethylbutyl ALA ester, substituted benzyl ALA ester, p-methylbenzyl ALA ester, p-nitrobenzyl ALA ester, p-[trifluoromethyl]benzyl ALA ester or p-fluorobenzyl ALA ester.

22. The kit of claim 8, wherein $R^2$ in said compound are both hydrogen atoms.

23. The kit of claim 22, wherein the compound is 2-methylpentyl ALA ester, 4-methyl pentyl ALA ester, 1-ethylbutyl ALA ester, substituted benzyl ALA ester, p-methylbenzyl ALA ester, p-nitrobenzyl ALA ester, p-[trifluoromethyl]henzyl ALA ester or p-fluorobenzyl ALA ester.

24. The method of claim 9, wherein $R^2$ in said compound are both hydrogen atoms.

25. The method of claim 24, wherein the compound is 2-methylpentyl ALA ester, 4-methyl pentyl ALA ester, 1-ethylbutyl ALA ester, substituted benzyl ALA ester, p-methylbenzyl ALA ester, p-nitrobenzyl ALA ester, p-[trifluoromethyl]benzyl ALA ester or p-fluorobenzyl ALA ester.

26. A method of diagnosis or photochemotherapeutic treatment of disorders or abnormalities of external or internal surfaces of the body, comprising:
a) administering to said external or internal surfaces, a composition comprising a compound of formula I,

$$R^2{}_2N\text{—}CH_2COCH_2\text{—}CH_2CO\text{—}OR^1 \qquad (I)$$

wherein $R^1$ represents
an optionally substituted branched non-cyclic $C_{6-30}$ alkyl group, or
a substituted alkyl group,
wherein said substituents are selected from hydroxy, alkoxy, acyloxy, alkoxycarbonyloxy, amino, aryl, nitro, oxo or fluoro groups,
and said alkyl group is optionally interrupted or terminated by one or more —O—, $NR^3$—, —S— or $PR^3$— groups;
$R^2$, each of which may be the same or different, represents a hydrogen atom or a group $R^1$,
wherein $R^1$ represents
an optionally substituted branched $C_{5-30}$ alkyl group, or
a substituted alkyl group,
wherein said substituents are selected from hydroxy, alkoxy, acyloxy, alkoxycarbonyloxy, amino, aryl, nitro, oxo or fluoro groups,
and said alkyl group is optionally interrupted or terminated by one or more —O—, $NR^3$—, —S— or $PR^3$— groups;
and $R^3$ represents a hydrogen or $C_{1-6}$ alkyl group,
or a pharmaceutically acceptable salt thereof, and at least one pharmaceutical carrier or excipient; and
b) exposing said external or internal surfaces to light.

27. The method of claim 26, wherein $R^1$ in said compound represents an optionally substituted branched nonyclic $C_{6-30}$ alkyl group, comprising a straight chain $C_{4-29}$ alkyl group, branched by substitution with one or more $C_{1-6}$ alkyl groups, wherein said site of substitution is at C2 or a higher C atom, or
an acyl or alkoxy substituted alkyl group.

28. The method of claim 26 or 27, wherein the light is in the wavelength region 300–800 nm.

29. The method of claim 26 or 27, wherein the composition further comprises at least one surface-penetration assisting agent and optionally one or more chelating agents.

30. The method of claim 26 or 27, wherein the compound is 2-methylpentyl ALA ester, 4-methyl pentyl ALA ester, 1-ethylbutyl ALA ester, benzyl ALA ester, p-methylbenzyl ALA ester, p-nitrobenzyl ALA ester, p-[trifluoromethyl] benzyl ALA ester or p-fluorobenzyl ALA ester.

31. A method of in vitro diagnosis, of abnormalities or disorders by assaying a sample of body fluid or tissue of a patient, said method comprising at least the following steps:
i) admixing said body fluid or tissue with a composition comprising a compound of formula I,

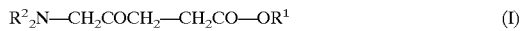

$$R^2{}_2N\text{—}CH_2COCH_2\text{—}CH_2CO\text{—}OR^1 \qquad (I)$$

wherein $R^1$ represents
an optionally substituted branched noncyclic $C_{6-30}$ alkyl group, or
a substituted alkyl group,
wherein said substituents are selected from hydroxy, alkoxy, acyloxy, alkoxycarbonyloxy, amino, aryl, nitro, oxo or fluoro groups,
and said alkyl group is optionally interrupted or terminated by one or more —O—, $NR^3$—, —S— or $PR^3$— groups;
$R^2$, each of which may be the same or different, represents a hydrogen atom or a group $R^1$,
wherein $R^1$ represents
an optionally substituted branched $C_{5-30}$ alkyl group, or
a substituted alkyl group,
wherein said substituents are selected from hydroxy, alkoxy, acyloxy, alkoxycarbonyloxy, amino, aryl, nitro, oxo or fluoro groups,
and said alkyl group is optionally interrupted or terminated by one or more —O—, $NR^3$—, —S— or $PR^3$— groups;
and $R^3$ represents a hydrogen or $C_{1-4}$ alkyl group,
or a pharmaceutically acceptable salt thereof, and at least one pharmaceutical carrier or excipient compound;
ii) exposing said mixture to light,
iii) ascertaining the level of fluorescence, and
iv) comparing the level of fluorescence to control levels.

32. The method of claim 31, wherein $R^1$ in said compound represents an optionally substituted branched non-cyclic $C_{6-30}$ alkyl group, comprising a straight chain $C_{4-29}$ alkyl group, branched by substitution with one or more $C_{1-6}$ alkyl groups, wherein said site of substitution is at C2 or a higher C atom, or
an acyl or alkoxy substituted alkyl group.

33. The method of claim 31 or 32, wherein the compound comprises is 2-methylpentyl ALA ester, 4-methyl pentyl ALA ester, 1-ethylbutyl ALA ester, benzyl ALA ester, p-methylbenzyl ALA ester, p-nitrobenzyl ALA ester, p-[trifluoromethyl]benzyl ALA ester or p-fluorobenzyl ALA ester.

34. A kit for use in photochemotherapy of disorders or abnormalities of external or internal surfaces of the body comprising:
a) a first container containing a compound of formula I,

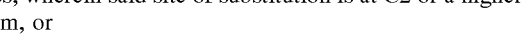

$$R^2{}_2N\text{—}CH_2COCH_2\text{—}CH_2CO\text{—}OR^1 \qquad (I)$$

wherein $R^1$ represents
an optionally substituted branched non-cyclic $C_{6-30}$ alkyl group, or
a substituted alkyl group,
wherein said substituents arc selected from hydroxy, alkoxy, acyloxy, alkoxycarbonyloxy, amino, aryl, nitro, oxo or fluoro groups, and said alkyl group is optionally interrupted or terminated by one or more —O—, NRC—, —S— or PR³— groups;

R², each of which may be the same or different, represents a hydrogen atom or a group R¹, wherein R¹ represents an optionally substituted branched $C_{5-30}$ alkyl group, or a substituted alkyl group, wherein said substituents are selected from hydroxy, alkoxy, acyloxy, alkoxycarbonyloxy, amino, aryl, nitro, oxo or fluoro groups, and said alkyl group is optionally interrupted or terminated by one or more —O—, NR³—, —S— or PR³— groups;

and R³ represents a hydrogen or $C_{1-6}$ alkyl group, or a pharmaceutically acceptable salt thereof, b) a second container containing at least one surface penetration assisting agent; and optionally c) one or more chelating agents contained either within said first container or in a third container.

35. The kit of claim 34, wherein R¹ in said compound represents an optionally substituted branched non-cyclic $C_{6-30}$ alkyl group, comprising a straight chain $C_{4-29}$ alkyl group, branched by substitution with one or more $C_{1-6}$ alkyl groups, wherein said site of substitution is at C2 or a higher C atom, or an acyl or alkoxy substituted alkyl group.

36. The kit of claim 34 or 35, wherein the compound is 2-methylpentyl ALA ester, 4-methyl pentyl ALA ester, 1-ethylbutyl ALA ester, benzyl ALA ester, p-methylbenzyl ALA ester, p-nitrobenzyl ALA ester, p-[trifluoromethyl]benzyl ALA ester or p-fluorobenzyl ALA ester.

37. A pharmaceutical composition comprising a therapeutically or diagnostically effective amount of a compound of formula I,

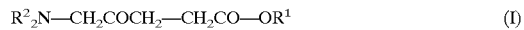

R²₂N—CH₂COCH₂—CH₂CO—OR¹     (I)

wherein

R¹ represents an optionally substituted branched non-cyclic $C_{6-30}$ alkyl group, or a substituted alkyl group, wherein said substituents are selected from hydroxy, alkoxy, acyloxy, alkoxycarbonyloxy, amino, aryl, nitro, oxo or fluoro groups, and said alkyl group is optionally interrupted or terminated by one or more —O—, NR³—, —S— or PR³— groups;

R², each of which may be the same or different, represents a hydrogen atom or a group R¹, wherein R¹ represents an optionally substituted branched $C_{5-30}$ alkyl group, or a substituted alkyl group, wherein said substituents are selected from hydroxy, alkoxy, acyloxy, alkoxycarbonyloxy, amino, aryl, nitro, oxo or fluoro groups, and said alkyl group is optionally interrupted or terminated by one or more —O—, NR³—, —S— or PR³— groups;

and R³ represents a hydrogen or $C_{1-6}$ alkyl group;

or a pharmaceutically acceptable salt thereof, and at least one pharmaceutical carrier or excipient.

38. The pharmaceutical composition of claim 37, wherein R¹ in said compound represents an optionally substituted branched non-cyclic $C_{6-30}$ alkyl group, comprising a straight chain $C_{4-29}$ alkyl group, branched by substitution with one or more $C_{1-6}$ alkyl groups, wherein said site of substitution is at C2 or a higher C atom, or an acyl or alkoxy substituted alkyl group.

39. The pharmaceutical composition of claim 38, wherein the optionally substituted branched non-cyclic $C_{6-30}$ alkyl group is a $C_{6-9}$ alkyl group.

40. The pharmaceutical composition of claim 38, wherein the straight chain $C_{4-29}$ alkyl group is a $C_{5-8}$ alkyl group.

41. The pharmaceutical composition of claim 38, wherein the one or more $C_{1-6}$ alkyl groups is a $C_1$ or $C_2$.

42. The pharmaceutical composition of claim 38, wherein the acyl or alkoxy substituted alkyl group is a $C_1$ or $C_2$ alkyl group.

43. The pharmaceutical composition of claim 42, wherein the acyl group is substituted.

44. The pharmaceutical composition of claim 43, wherein the acyl group is substituted with one or more alkyl, fluoro or nitro groups.

45. The pharmaceutical composition of claim 44, wherein the one or more alkyl groups are substituted.

46. The pharmaceutical composition of claim 38, wherein the alkoxy group is substituted by one or more alkoxy groups.

47. The pharmaceutical composition of claim 46, wherein the one or more alkoxy groups are substituted.

48. The pharmaceutical composition of claim 37 or 38, wherein R² in said compound are both hydrogen atoms.

49. The pharmaceutical composition of claim 48, wherein the compound is 2-methylpentyl ALA ester, 4-methyl pentyl ALA ester, 1-ethylbutyl ALA ester, benzyl ALA ester, p-methylbenzyl ALA ester, p-nitrobenzyl ALA ester, p-[trifluoromethyl]benzyl ALA ester or p-fluorobenzyl ALA ester.

50. A product comprising the pharmaceutical composition of claim 37 or 38, at least one surface-penetration assisting agent, and optionally one or more chelating agents as a combined preparation for simultaneous, separate or sequential use in treating disorders or abnormalities of external or internal surfaces of the body which are responsive to photochemotherapy.

51. The product of claim 52, wherein R² in said compound are both hydrogen atoms.

52. The product of claim 51, wherein the compound is 2-methylpentyl ALA ester, 4-methyl pentyl ALA ester, 1-ethylbutyl ALA ester, benzyl ALA ester, p-methylbenzyl ALA ester, p-nitrobenzyl ALA ester, >[trifluoromethyl]benzyl ALA ester or p-fluorobenzyl ALA ester.

* * * * *